US012727838B2

(12) United States Patent
Yu et al.

(10) Patent No.: US 12,727,838 B2

(45) Date of Patent: Sep. 8, 2026

(54) ORAL CONE BEAM X-RAY IMAGING SYSTEM AND FAST POSITIONING METHOD THEREFOR

(71) Applicant: Yofo Medical Technology Co., Ltd., Anhui (CN)

(72) Inventors: Wenrui Yu, Anhui (CN); Yunyan Cai, Anhui (CN); Ran Xu, Anhui (CN); Zhe Liu, Anhui (CN)

(73) Assignee: Yofo Medical Technology Co., Ltd., Anhui (CN)

( * ) Notice: Subject to any disclaimer, the term of this patent is extended or adjusted under 35 U.S.C. 154(b) by 144 days.

(21) Appl. No.: 18/670,656

(22) Filed: May 21, 2024

(65) Prior Publication Data

US 2024/0389963 A1 Nov. 28, 2024

Related U.S. Application Data

(63) Continuation of application No. PCT/CN2022/133641, filed on Nov. 23, 2022.

(30) Foreign Application Priority Data

Nov. 24, 2021 (CN) ........................ 202111404653.2
Nov. 7, 2022 (CN) ........................ 202211387129.3

(51) Int. Cl.

*A61B 6/51* (2024.01)
*A61B 6/00* (2006.01)
(Continued)

(52) U.S. Cl.

CPC ................ *A61B 6/51* (2024.01); *A61B 6/032* (2013.01); *A61B 6/4085* (2013.01);
(Continued)

(58) Field of Classification Search

CPC ......... A61B 6/51; A61B 6/032; A61B 6/4085; A61B 6/4441; A61B 6/5205;
(Continued)

(56) References Cited

U.S. PATENT DOCUMENTS

| | | | |
|---|---|---|---|
| 12,014,449 B2 * | 6/2024 | Chukalina ............ | G06T 11/005 |
| 2009/0323891 A1 | 12/2009 | Borghese et al. | |
| 2015/0164446 A1 | 6/2015 | Toimela | |

FOREIGN PATENT DOCUMENTS

| | | | |
|---|---|---|---|
| CN | 101668485 | 3/2010 | |
| CN | 101668485 A * | 3/2010 | ............ A61B 6/488 |

(Continued)

OTHER PUBLICATIONS

"International Search Report (Form PCT/ISA/210) of PCT/CN2022/133641," mailed on Jan. 28, 2023 with English translation thereof, pp. 1-6.

(Continued)

*Primary Examiner* — Uzma Alam
*Assistant Examiner* — Fani Polyzos Boosalis
(74) *Attorney, Agent, or Firm* — JCIPRNET

(57) ABSTRACT

The present disclosure provides an oral cone beam X-ray imaging system and its fast positioning method. The working modes of the imaging system includes an oral CT shooting mode, an oral panoramic shooting mode, and a head frontal and lateral shooting mode. The system includes a source, a flat panel detector, a rotating driving device, a data processing device, and a control device. The number of sources, flat panel detectors, and rotating driving devices is one to form a single-path imaging system. The working mode also includes a fast positioning mode to perform Self-Adaptation positioning of the imaging system based on the positioning result of the fast positioning mode. In the rapid positioning method, low-dose X-rays are emitted; CT (Continued)

images are received and reconstructed to obtain the current pose of the measured object; and based on the current pose, the imaging system performs Self-Adaptation positioning to perform imaging in the oral panoramic shooting mode or the head lateral shooting mode.

19 Claims, 16 Drawing Sheets

(51) Int. Cl.

| | |
|---|---|
| ***A61B 6/03*** | (2006.01) |
| ***A61B 6/40*** | (2024.01) |
| ***G06T 5/70*** | (2024.01) |
| ***G06T 7/11*** | (2017.01) |
| ***G06T 7/136*** | (2017.01) |
| ***G06T 7/60*** | (2017.01) |
| ***G06T 7/70*** | (2017.01) |
| ***G06T 12/00*** | (2026.01) |

(52) U.S. Cl.
CPC .......... *A61B 6/4441* (2013.01); *A61B 6/5205* (2013.01); *A61B 6/5229* (2013.01); *A61B 6/54* (2013.01); *G06T 5/70* (2024.01); *G06T 7/11* (2017.01); *G06T 7/136* (2017.01); *G06T 7/60* (2013.01); *G06T 7/70* (2017.01); *G06T 12/00* (2026.01); *G06T 2200/04* (2013.01); *G06T 2207/10081* (2013.01); *G06T 2207/10116* (2013.01); *G06T 2207/20084* (2013.01); *G06T 2207/30008* (2013.01); *G06T 2207/30036* (2013.01); *G06T 2210/41* (2013.01)

(58) Field of Classification Search
CPC ......... A61B 6/5229; A61B 6/54; G06T 7/136; G06T 7/11; G06T 7/70; G06T 5/70; G06T 12/00; G06T 7/60; G06T 2200/04; G06T 2207/10081; G06T 2207/10116; G06T 2207/20084; G06T 2207/30008; G06T 2207/30036; G06T 2210/41
See application file for complete search history.

(56) References Cited

FOREIGN PATENT DOCUMENTS

| | | | | |
|---|---|---|---|---|
| CN | 101933813 | | 1/2011 | |
| CN | 204274493 | | 4/2015 | |
| CN | 210077687 | | 2/2020 | |
| CN | 113069141 | | 7/2021 | |
| CN | 113069141 A | * | 7/2021 | ........... A61B 6/4429 |
| CN | 114081524 | | 2/2022 | |
| CN | 114081524 A | * | 2/2022 | ............... A61B 6/54 |

OTHER PUBLICATIONS

"Written Opinion of the International Searching Authority (Form PCT/ISA/237) of PCT/CN2022/133641," mailed on Jan. 28, 2023, pp. 1-7.

* cited by examiner

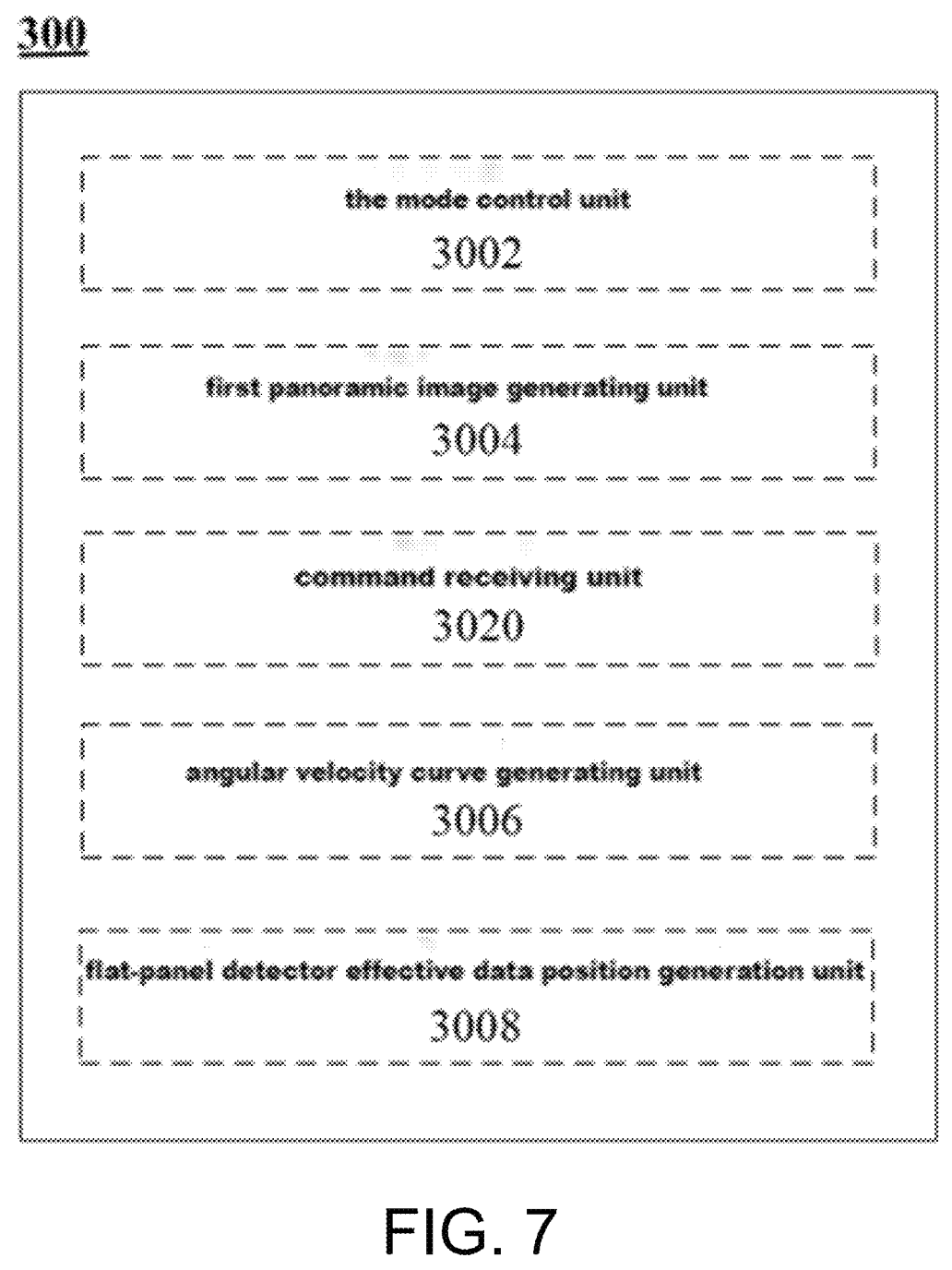

300 the mode control unit
3002 first panoramic image generating unit
3004 command receiving unit
3020 angular velocity curve generating unit
3006 flat-panel detector effective data position generation unit
3008

FIG. 7

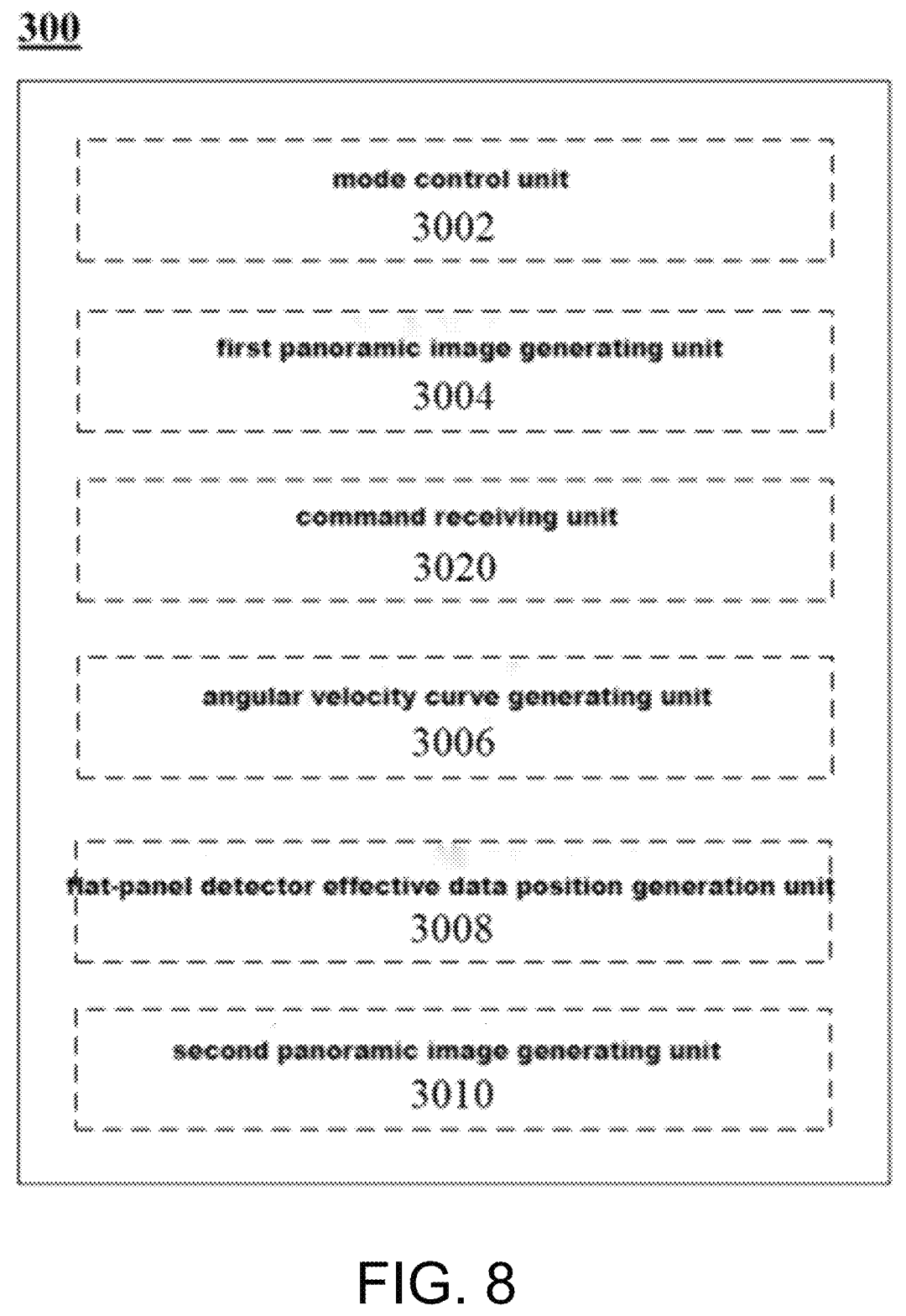

300 mode control unit
3002 first panoramic image generating unit
3004 command receiving unit
3020 angular velocity curve generating unit
3006 flat-panel detector effective data position generation unit
3008 second panoramic image generating unit
3010

FIG. 8

ORAL CONE BEAM X-RAY IMAGING SYSTEM AND FAST POSITIONING METHOD THEREFOR

CROSS-REFERENCE TO RELATED APPLICATION

This application is a continuation of international application of PCT application serial no. PCT/CN2022/133641, filed on Nov. 23, 2022, which claims the priority benefit of China application no. 202111404653.2, filed on Nov. 24, 2021 and application No. 202211387129.3, filed on Nov. 7, 2022. The entirety of each of the above-mentioned patent applications is hereby incorporated by reference herein and made a part of this specification.

TECHNICAL FIELD

The present disclosure relates to an oral cone-beam X-ray imaging system and its rapid positioning method.

TECHNICAL BACKGROUND

Conventional oral X-ray imaging encompasses four main modalities: oral CT scanning, panoramic dental imaging, cranial lateral imaging, and dental film imaging. The integration of oral CT scanning, panoramic imaging, and cranial lateral imaging into a single system is currently the mainstream solution in oral X-ray imaging systems, commonly referred to as a three-in-one oral imaging system.

Oral CT scanning typically involves a 360° circular trajectory rotation scan followed by three-dimensional reconstruction to obtain oral CT data. During the 360° rotation scan, several hundred to over a thousand projections are required. Each projection has a limited exposure time, resulting in a limited X-ray radiation dose per projection. To increase the radiation dose received by the flat-panel detector, a shorter source-to-detector distance (SID) of generally 500 to 1000 mm is commonly employed.

In contrast to the 360° circular trajectory rotation scan of oral CT scanning, oral panoramic imaging uses a fixed relative position between the source and detector. It employs a three-segment arc motion trajectory where the rotational center of the arc moves according to a specified rule. Similarly, several hundred to over a thousand projections are taken during the motion, followed by reconstruction using tomographic principles. Therefore, like oral CT scanning, oral panoramic imaging faces limitations on the source-to-detector distance due to radiation dose considerations, typically ranging from 500 to 1000 mm.

Cranial lateral imaging, on the other hand, involves two-dimensional direct imaging with significantly lower dose requirements compared to oral CT and panoramic imaging. To ensure minimal distortion in each imaging position, cranial lateral imaging requires a sufficiently large source-to-detector distance, typically exceeding 1700 mm.

Given these considerations, current mainstream three-in-one technologies use two optical paths to simultaneously achieve oral CT scanning, panoramic imaging, and cranial lateral imaging. One optical path maintains a source-to-detector distance of 500 to 1000 mm for oral CT scanning and panoramic imaging. Oral CT scanning utilizes a fixed rotation center circular trajectory, while oral panoramic imaging uses a fixed relative position between the source and detector, moving the rotation center during imaging to achieve panoramic imaging. The second optical path reuses the source from the first path and combines it with a linear array detector or a large-size flat panel detector (e.g., 40 cm×30 cm), achieving a source-to-detector distance of over 1700 mm for cranial lateral imaging.

Existing three-in-one systems employing two optical paths to achieve oral CT scanning, panoramic imaging, and cranial lateral imaging simultaneously incur high system costs and complexity. The image quality of oral panoramic imaging depends significantly on the correlation between the patient's actual dental arch curve and the preset dental arch curve. Although multiple sets of preset dental arch curves can be used, the diversity of individual dental arches limits the effectiveness of this approach. Moreover, the positioning process during oral panoramic imaging is cumbersome. Despite cranial lateral imaging being a two-dimensional process, its clinical demand imposes strict requirements for positioning, such as aligning the X-ray source, left ear canal, and right ear canal in a straight line without tilting the skull. Typically, achieving the correct positioning for cranial lateral imaging can take several minutes or even more than ten minutes, significantly affecting imaging efficiency and patient experience.

SUMMARY OF THE INVENTION

The present disclosure provides a cone-beam X-ray imaging system for oral applications, comprising the following operating modes: oral CT imaging mode, panoramic dental imaging mode, and cranial lateral imaging mode. The system includes: an X-ray source configured to emit cone-beam X-rays towards the subject; a flat-panel detector configured to detect the X-rays passing through the subject; a rotational driving device configured to rotate the X-ray source and the flat-panel detector, or to rotate the subject; a data processing device configured to receive operational mode commands to select a set of control parameters corresponding to one of the oral CT imaging mode, panoramic dental imaging mode, and cranial lateral imaging mode; and a control device configured to receive the selected set of control parameters, control the rotational driving device, and/or control the X-ray source and the flat-panel detector to perform imaging, wherein the number of the X-ray source, the flat-panel detector, and the rotational driving device is one, so as to form a single imaging pathway system.

The present disclosure also provides a rapid positioning method based on a cone-beam X-ray imaging system for oral applications, comprising: initiating the rapid positioning mode, emitting low-dose X-rays; receiving and reconstructing CT images to obtain the current position and posture of the subject; and based on the current position and posture, the imaging system performs adaptive positioning to facilitate imaging in either the panoramic dental imaging mode or the cranial lateral imaging mode.

BRIEF DESCRIPTION OF THE DRAWINGS

The drawings illustrate exemplary embodiments of the present disclosure and, together with the description, serve to explain the principles of the present disclosure. The drawings are included to provide further understanding of the present disclosure and form a part of this specification.

FIG. 7 is a schematic diagram of the data processing device according to an embodiment of the present disclosure.

FIG. 8 is a schematic diagram of the data processing device according to an embodiment of the present disclosure.

DETAILED DESCRIPTION OF THE EMBODIMENTS

Figure 1:
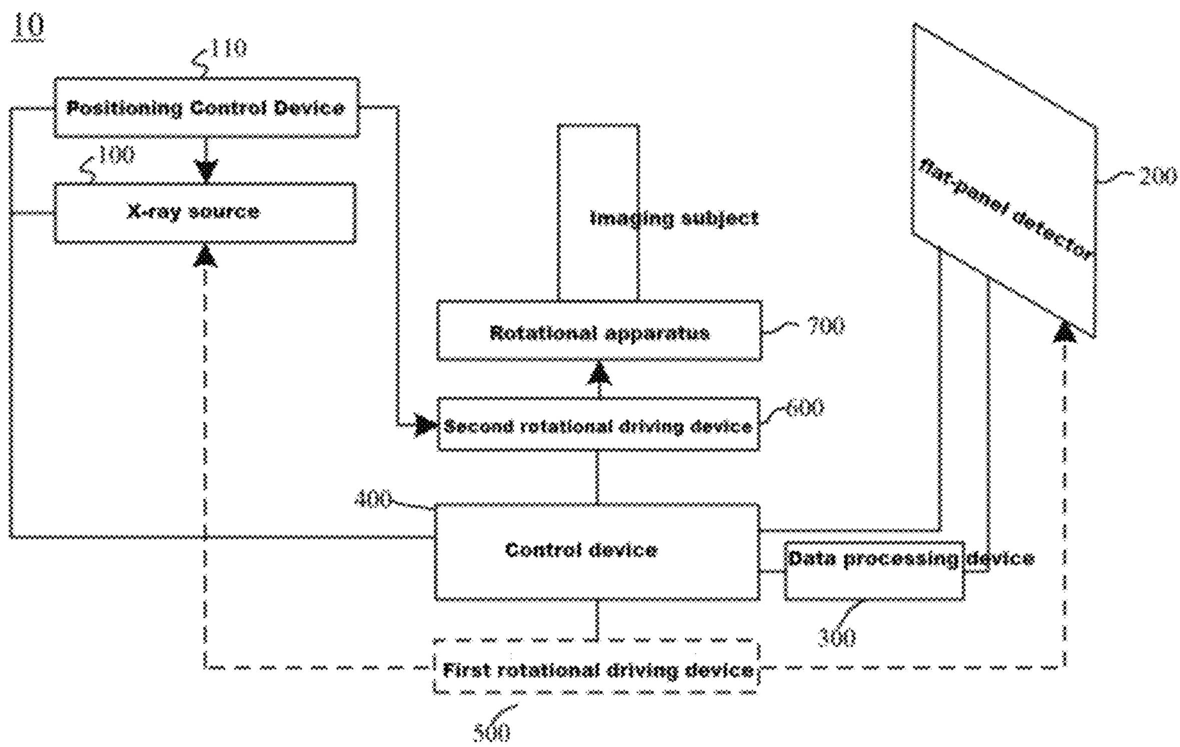
FIG. 1 is a schematic diagram of a cone-beam X-ray imaging system according to an embodiment of the present disclosure.

The present disclosure is further described in detail below with reference to the accompanying drawings and embodiments. It should be understood that the specific embodiments described herein are merely for explanation purposes and are not intended to limit the present disclosure. Additionally, for the sake of clarity, only parts related to the present disclosure are shown in the drawings.

It should be noted that, as long as there is no conflict, the embodiments and the features within the embodiments described in the present disclosure can be combined with each other. The technical solutions of the present disclosure will be described in detail below with reference to the accompanying drawings and specific embodiments.

Unless otherwise stated, the exemplary embodiments/examples shown should be understood as illustrative of various detailed features that can be implemented in practice according to the technical concepts of the present disclosure. Therefore, unless otherwise stated, features of the various embodiments/examples can be combined, separated, interchanged, and/or rearranged without departing from the technical concepts of the present disclosure.

FIG. 1 is a schematic structural diagram of a cone beam X-ray imaging system according to an embodiment of the present disclosure. The cone beam X-ray imaging system 10 of the present disclosure can operate in an oral CT imaging mode, an oral panoramic imaging mode, and a cephalometric imaging mode. In the oral CT imaging mode, imaging is performed by following a circular trajectory motion to capture images and then performing three-dimensional reconstruction. The oral panoramic imaging mode can include a first oral panoramic imaging mode or a second oral panoramic imaging mode. In the first oral panoramic imaging mode, variable-speed rotation imaging is performed based on a circular trajectory, and multi-rotation center oral panoramic imaging is achieved through reordering processing. In the second oral panoramic imaging mode, constant-speed rotation imaging is performed based on a circular trajectory, and oral panoramic imaging is achieved through interpolation processing. In the cephalometric imaging mode, anteroposterior and lateral cephalometric images are obtained based on circular trajectory motion. Additionally, the imaging system 10 may include a rapid positioning mode. This rapid positioning mode is used for adaptive positioning of the imaging system. For example, when selecting the oral panoramic imaging mode or the cephalometric imaging mode, the rapid positioning mode is first initiated. In this rapid positioning mode, the imaging trajectory of the oral CT imaging mode is used, and the radiation dose of the X-rays is lower than that in the oral CT imaging mode, so as to perform adaptive positioning of the imaging system based on the positioning results of the rapid positioning mode.

Referring to FIG. 1, the imaging system 10 of the present disclosure may include an X-ray source 100, a flat-panel detector 200, a data processing device 300, a control device 400, and a rotational driving device. The X-ray source 100 is configured to emit a cone beam of X-rays towards the subject being examined. The flat-panel detector 200 is designed to detect the X-rays that have passed through the subject. The flat-panel detector 200 may be a flat panel detector, preferably a rectangular flat panel detector or a small flat panel detector. The X-ray imaging locations can include the head, jaw, and oral cavity of the human body. The rotational driving device may include a first rotational driving device 500 or a second rotational driving device 600. In cases where the rotational driving device includes the first rotational driving device 500, it can synchronously drive both the X-ray source 100 and the flat-panel detector 200 in a circular trajectory around the subject (patient), while the subject remains stationary. In cases where the rotational driving device includes the second rotational driving device 600, it can control the rotation of the subject while the X-ray source and flat-panel detector remain fixed. The second rotational driving device 600 drives the rotational apparatus 700, causing the subject positioned on the rotational apparatus 700 to move, thereby enabling the X-ray source 100 and the flat-panel detector 200 to perform imaging along a circular trajectory. The control device 400 can be used to control the first rotational driving device or the second rotational driving device, as well as to control the X-ray source and flat-panel detector during imaging. In the present disclosure, it is preferable that the rotational driving device only includes the second rotational driving device 600, which controls the rotation of the subject for imaging.

Figure 2:
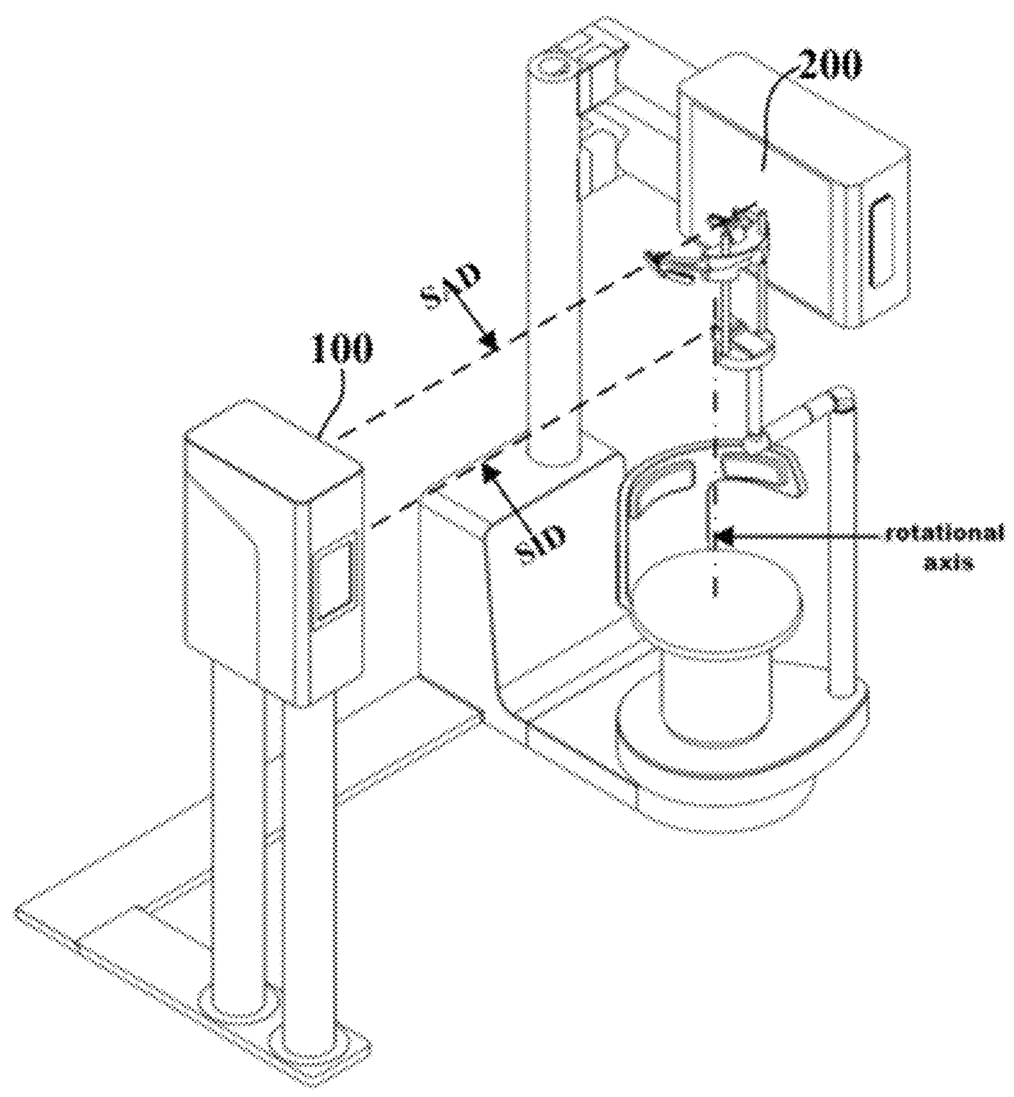
FIG. 2 is a schematic diagram of a cone-beam X-ray imaging system according to an embodiment of the present disclosure.

The X-ray source 100, flat-panel detector 200, and rotational driving device are each provided in a single unit, thus forming a single-path imaging system. The present disclosure adopts a floor-mounted structure as shown in FIG. 2 and includes a second rotational driving device to rotate the subject. For example, the second rotational driving device can drive a seat-type rotational apparatus, causing the subject seated on the seat to rotate, while the X-ray source 100 and flat-panel detector 200 remain stationary. As shown in FIG. 2, the distance between the X-ray source 100 and the flat-panel detector 200, referred to as the Source-to-Image Distance (SID), can be between 1.5 m and 2.5 m. The distance between the X-ray source 100 and the rotational axis is referred to as the Source-to-Axis Distance (SAD), with the difference between SID and SAD being 0.2 m to 0.4 m. Preferably, the SID is 1.7 m, and the difference between SID and SAD is 0.25 m.

Figure 3:
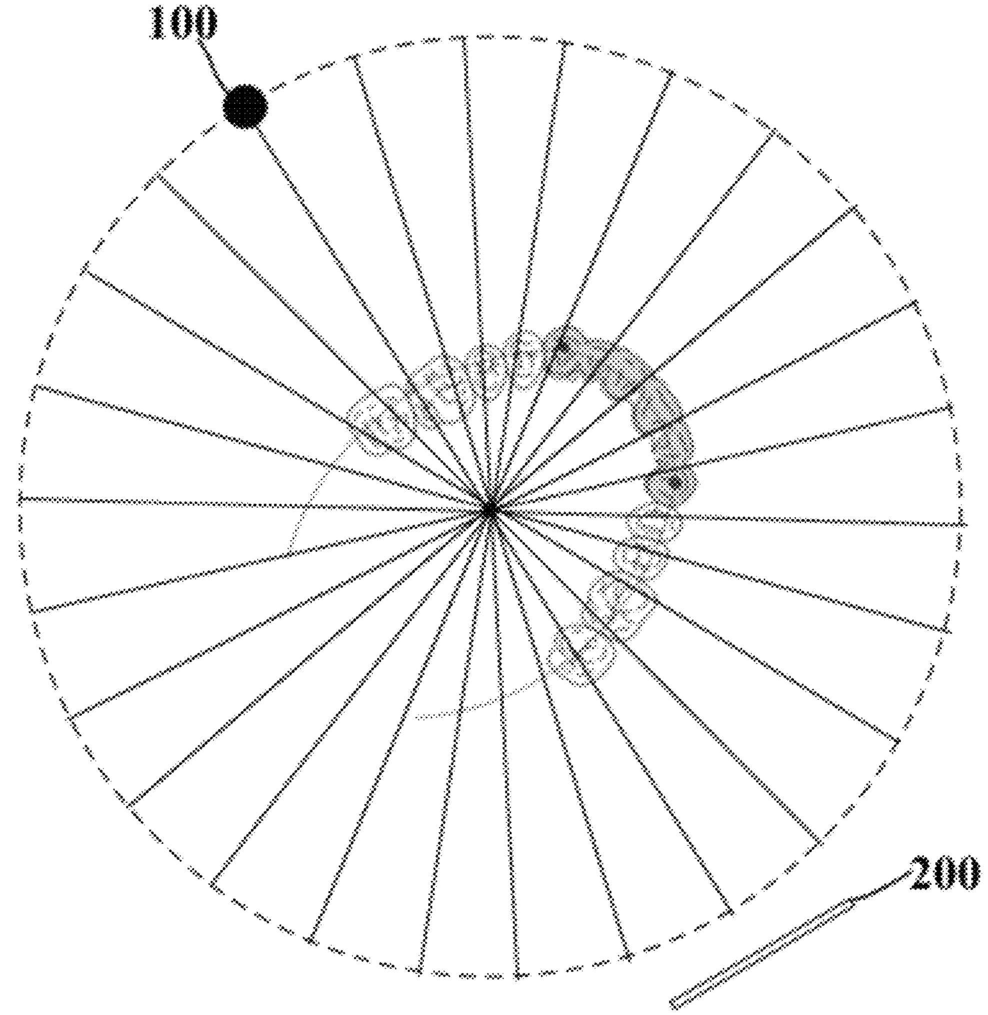
FIG. 3 is a schematic diagram of the operational mode for oral CT imaging according to an embodiment of the present disclosure.
Figure 4:
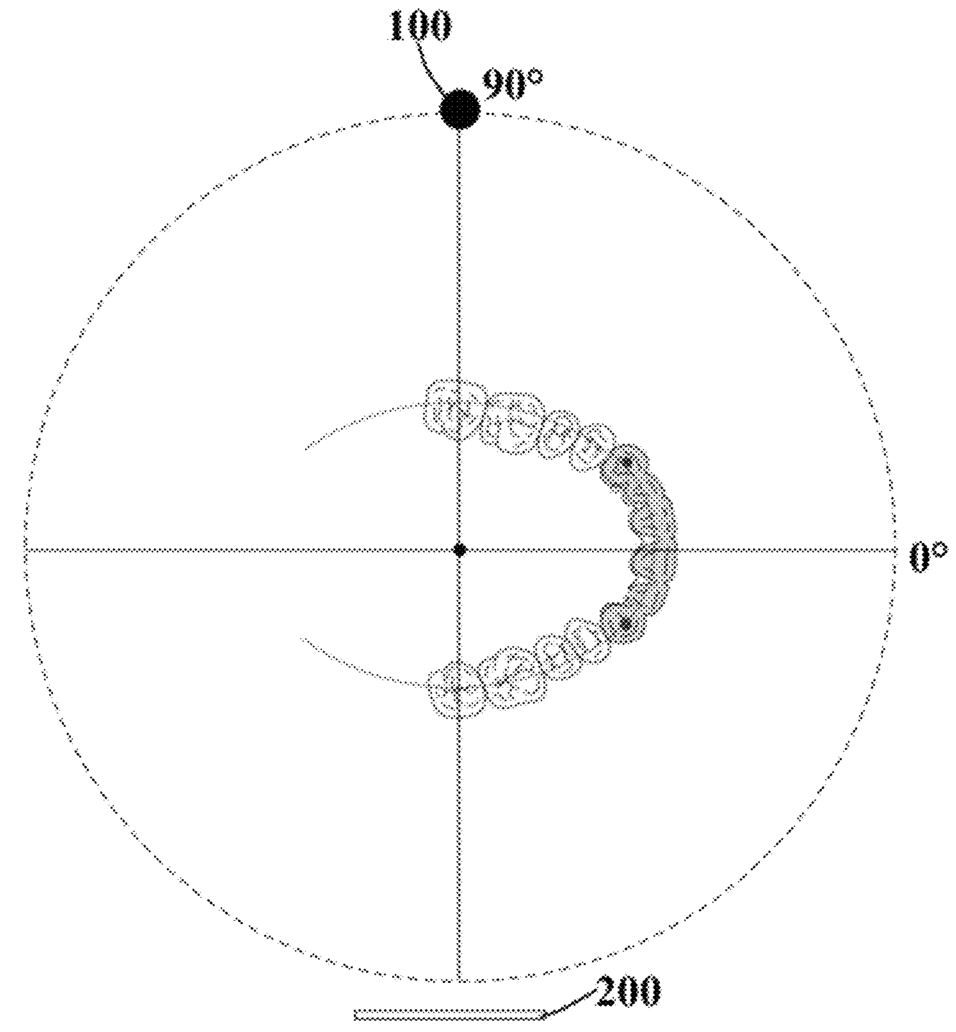
FIG. 4 is a schematic diagram of the operational mode for cranial lateral imaging according to an embodiment of the present disclosure.

According to an embodiment of the present disclosure, the X-ray imaging system can operate in oral CT imaging mode, oral panoramic imaging mode, and cephalometric imaging mode. When capturing images in the oral panoramic imaging mode and cephalometric imaging mode, the system can first perform a quick positioning mode. FIG. 3 illustrates a schematic view of the system operating in oral CT imaging mode. In this mode, the subject can rotate at a constant speed. In FIG. 3, the relative rotational path of the X-ray source is indicated by a dashed circular outline. As shown in FIG. 3, because the subject rotates, the X-ray source can be arranged to follow a circular trajectory relative to the subject. FIG. 4 illustrates a schematic view of the system operating in cephalometric imaging mode. As depicted in FIG. 4, the system can capture a frontal image at the 0° position and a lateral image at the 90° position. Here, 0° is defined as the angle perpendicular to the coronal plane of the head, and 90° is defined as a 90° rotation clockwise or counterclockwise from the 0° position.

Figure 5:
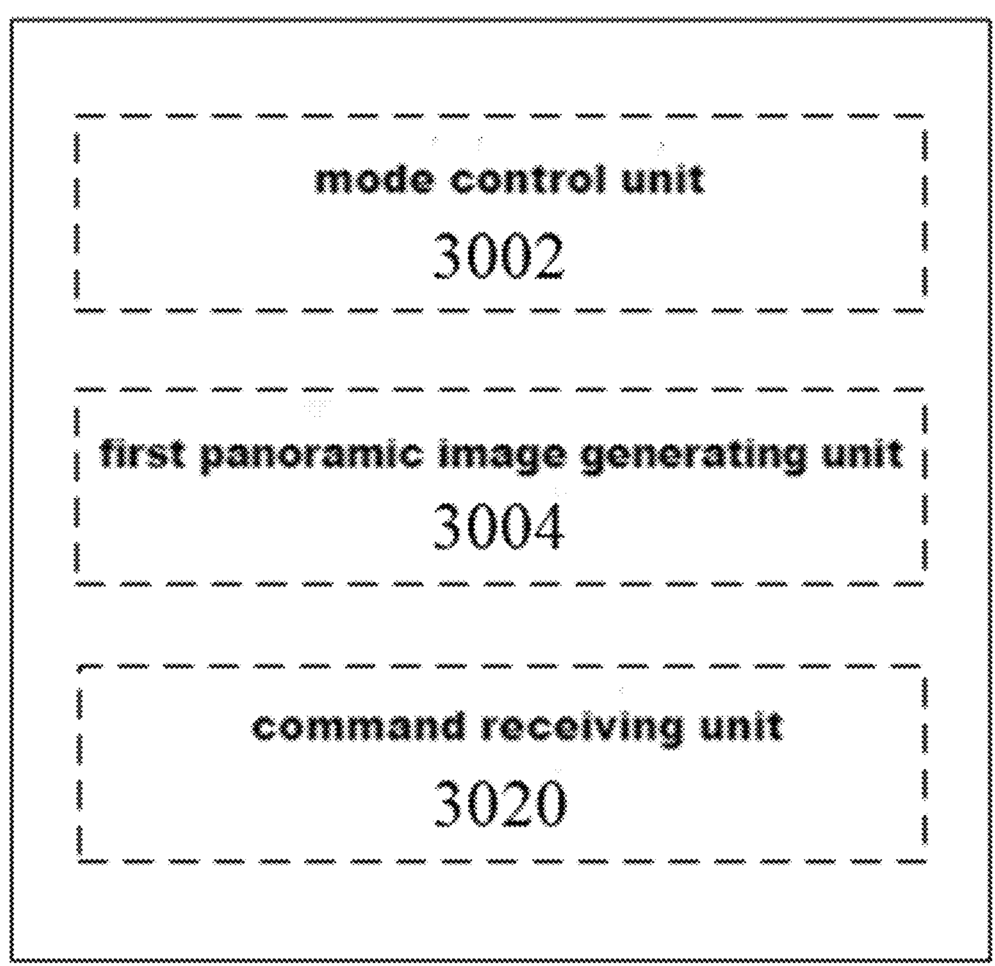
FIG. 5 is a schematic diagram of the data processing device according to an embodiment of the present disclosure.

For the oral panoramic imaging mode, either the first oral panoramic imaging mode or the second oral panoramic imaging mode can be used. FIG. 5 shows a schematic diagram of the data processing device for the first oral panoramic imaging mode. As shown in FIG. 5, the data processing device 300 may include a mode control unit 3002, a command receiving unit 3020, and a first panoramic image generating unit 3004. The command receiving unit 3020 receives the operational mode from an external source. The mode control unit 3002 retrieves the corresponding operational mode control parameter set based on the received operational mode command. The control device 400 controls the relative rotation between the subject, the X-ray source 100, and the flat-panel detector 200 based on the operational mode control parameter set retrieved by the mode control unit 3002, and also controls the X-ray source 100 and the flat-panel detector 200 to capture images. It should be noted that during oral CT imaging mode and cephalometric imaging mode, the command receiving unit 3020 receives external commands, and the mode control unit 3002 controls the system to perform oral CT imaging mode or cephalometric imaging mode.

Figure 6:
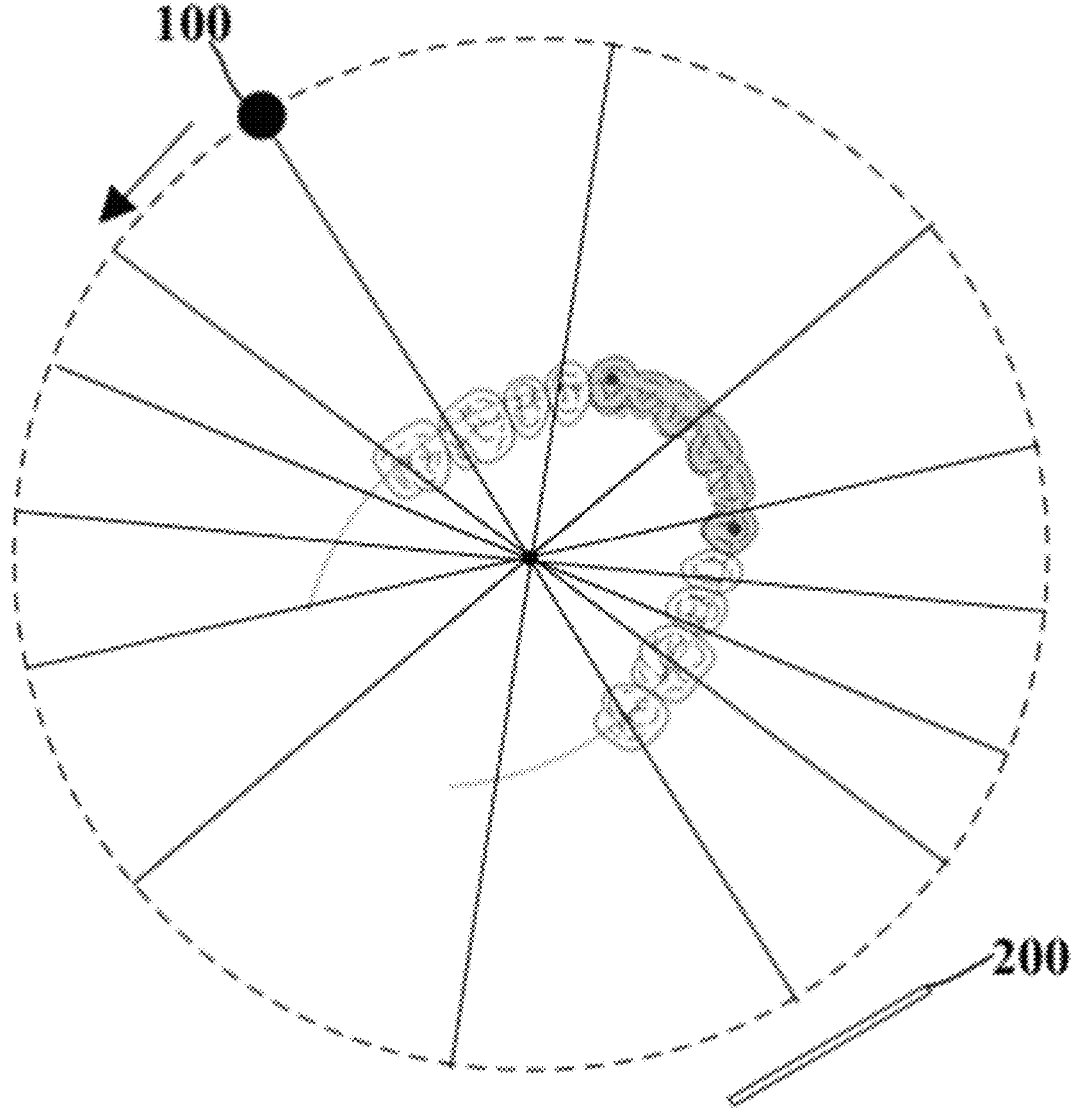
FIG. 6 is a schematic diagram of the first operational mode for panoramic dental imaging according to an embodiment of the present disclosure.

In the data processing device shown in FIG. 5, panoramic imaging can be achieved through the first oral panoramic imaging mode. In this first oral panoramic imaging mode, the subject is controlled to rotate at variable speeds, as illustrated in FIG. 6. The operational mode control parameter set includes at least the first oral panoramic imaging mode control parameter set. The first panoramic image generating unit 3004 rearranges the first sequence of two-dimensional projection data (i.e., a series of two-dimensional projection images) collected by the flat-panel detector 200 during the relative rotation process controlled by the first oral panoramic imaging mode control parameter set (the relative rotation process between the X-ray source 100, the flat-panel detector 200, and the subject) to generate the first panoramic image of the oral region. The relative rotation process controlled by the first oral panoramic imaging mode control parameter set is a variable speed rotation process.

The rearrangement process may include: arranging the first sequence of two-dimensional projection data based on at least the positional information of various imaging points in the oral region. Specifically, for each imaging point in the oral region, the positional information is used to obtain the corresponding position of the X-ray source. The projection position of each imaging point on the flat-panel detector is determined based on the X-ray source position corresponding to each imaging point, and the two-dimensional projection data at the projection positions of the various imaging points on the flat-panel detector (i.e., column data, where the width of the column data depends on the spacing between the various imaging points; preferably, the spacing between the imaging points is uniform) are selected and arranged to obtain the first panoramic image.

The angular velocity curve of the variable speed rotation process is generated based on the characteristic data of the oral region (preferably the shape characteristic data of the oral region, such as the dental arch curve), such that the rotation time between adjacent X-ray source positions corresponding to each imaging point is equal.

FIG. 7 illustrates a schematic diagram of the data processing device 300. The data processing device 300 may also include an angular velocity curve generation unit 3006 and a detector effective data position generation unit 3008. The angular velocity curve generation unit 3006 generates an angular velocity curve based on selected oral region feature data (e.g., the selected dental arch curve). The detector effective data position generation unit 3008 generates the detector effective data position based on selected oral region feature data (e.g., the selected dental arch curve).

The data processing device 300 may also include a memory. The memory can store various pre-generated dental arch curve data (i.e., oral region characteristic data). The angular velocity curve generating unit 3006 and the flat-panel detector effective data position generating unit 3008 generate the angular velocity curve and the flat-panel detector effective data positions based on the dental arch curve data selected by the oral region characteristic selection command. As an example, the first oral panoramic imaging mode control parameter set is generated based on at least the angular velocity curve and the flat-panel detector effective data positions. During the variable speed rotation process, the flat-panel detector 200 collects data at a preset acquisition rate to obtain the first sequence of two-dimensional projection data.

In the cone beam X-ray imaging system of the various embodiments described above, the variable speed rotation process may include at least one circumferential rotation process. The first panoramic image generating unit 3004 rearranges the first sequence of two-dimensional projection data (i.e., a series of two-dimensional projection images) collected by the flat-panel detector 200 during the relative rotation process controlled by the first oral panoramic imaging mode control parameter set (the relative rotation process between the X-ray source 100, the flat-panel detector 200, and the subject) to generate a first panoramic image with more than two rotation centers. Additionally, by rearranging a series of two-dimensional projection images, a first panoramic image with more than two rotation centers can be obtained.

The appropriate dental arch curve data can be selected based on the patient's facial shape and other factors. The X-ray imaging system generates the angular velocity curve and the flat-panel detector effective data positions for the imaging process based on the dental arch curve data. During imaging, the X-ray source 100 emits a cone beam of X-rays while the flat-panel detector 200 collects X-ray projection images at a certain acquisition rate as it moves in a circular trajectory around the patient's head (oral region) based on the generated angular velocity curve. Since the X-rays are in a cone beam and the flat-panel detector is a flat-panel detector, the projection lines form a certain angle with the center line between the X-ray source and the flat-panel detector. By rearranging the two-dimensional projection data, a multi-rotation center oral panoramic imaging effect can be achieved.

Figure 9:
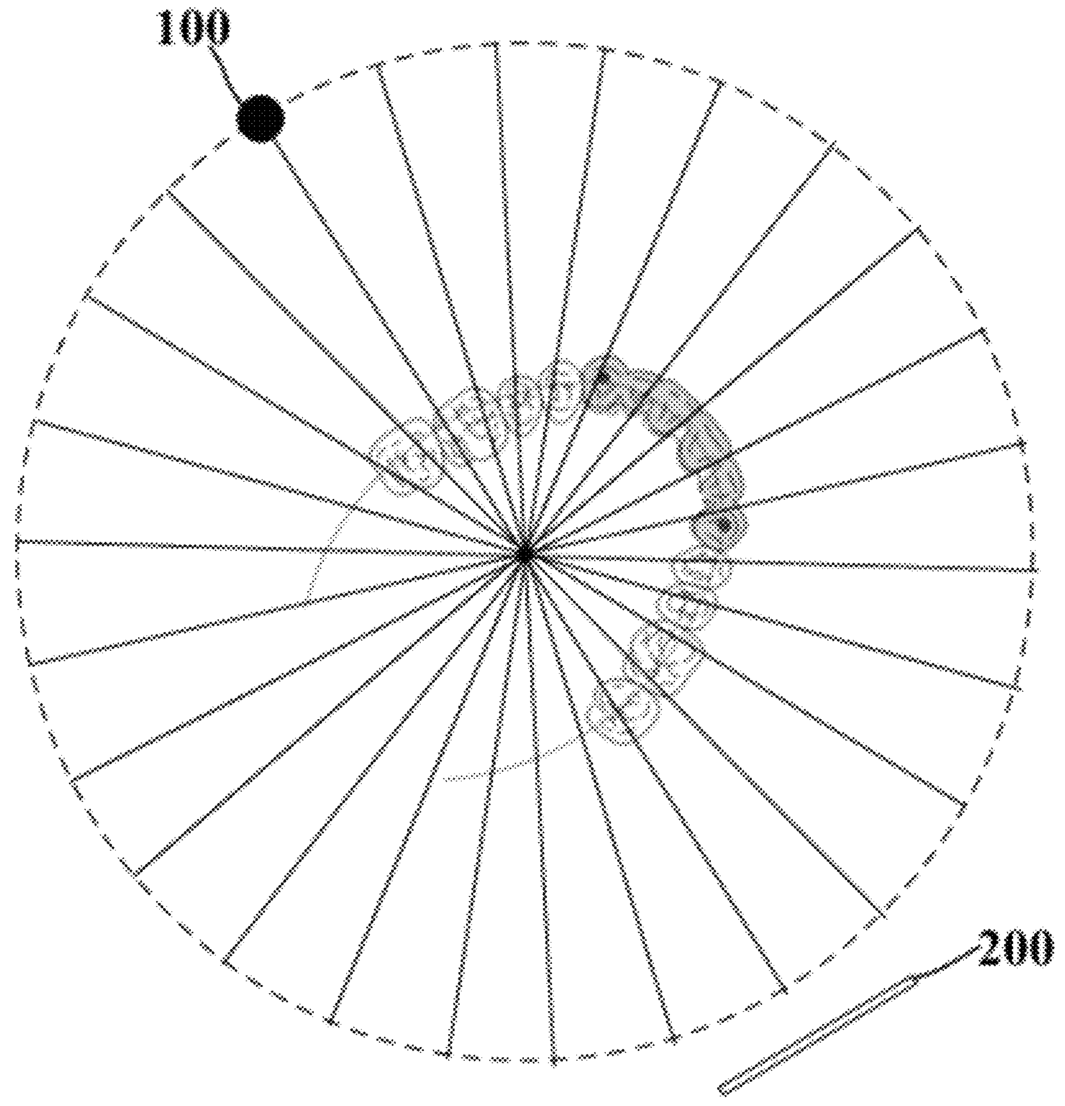
FIG. 9 is a schematic diagram of the second operational mode for panoramic dental imaging according to an embodiment of the present disclosure.

According to one embodiment of the present disclosure, the second oral panoramic imaging mode can be used as the panoramic image mode. For example, in the embodiment shown in FIG. 5, the second panoramic image generating unit may be used instead of the first panoramic image generating unit. Alternatively, both the first and second panoramic image generating units can be included. When the second panoramic image generating unit is included, the working mode control parameter set may include at least the second oral panoramic imaging mode control parameter set. The second panoramic image generating unit 3010 performs interpolation processing on the second sequence of two-dimensional projection data (i.e., a series of two-dimensional projection images) collected by the flat-panel detector 200 during the relative rotation process controlled by the second oral panoramic imaging mode control parameter set (the relative rotation process between the X-ray source 100, the flat-panel detector 200, and the subject) to generate the second panoramic image of the oral region. As shown in FIG. 9. The relative rotation process controlled by the second oral panoramic imaging mode control parameter set is a constant-speed rotation process. Preferably, the constant-speed rotation process includes at least one circumferential rotation process.

As an example, the interpolation processing may include: determining whether each X-ray source position of the flat-panel detector during the data acquisition process is the target position calculated based on the position information of each imaging point of the oral region; and if a certain X-ray source position is not the target position, performing weighted processing on the projection data collected at that X-ray source position based on the positional offset. The positional offset is the distance between the intersection point of the line connecting the X-ray source position and the rotation center with the oral region and the adjacent imaging point. The weighted projection data is then superimposed on the projection data corresponding to the adjacent imaging point (after processing all projection data, normalization is performed).

According to another example, the interpolation processing may include: calculating the target position of the X-ray source based on the position information of each imaging point of the oral region; and, if no projection data is collected at a certain target position of the X-ray source during the actual projection data collection process, obtaining the projection data at the target position based on the projection data collected at adjacent X-ray source positions corresponding to imaging points. The step of obtaining the projection data at the target position of the X-ray source may include: performing linear interpolation on the projection data collected at two or more adjacent X-ray source positions corresponding to imaging points to obtain the projection data at the target position of the X-ray source.

As described above, for the oral panoramic imaging mode, either the variable-speed first oral panoramic imaging mode or the constant-speed second oral panoramic imaging mode can be used.

In the variable-speed first oral panoramic imaging mode, the angular velocity curve of the imaging process can be generated according to the dental arch curve, and the subject can be made to perform circular or partial circular motion according to this angular velocity. In the constant-speed second oral panoramic imaging mode, the subject can be made to perform circular or partial circular motion at a constant speed. During the movement, the X-ray source can emit X-rays, and the flat-panel detector can collect data at a certain rate, eventually reconstructing the panoramic image.

In either the first or second oral panoramic imaging mode, the dental arch curve of the subject and the virtual rotation axis are first determined. The virtual rotation axis parameters are determined to minimize the impact of the contralateral bony structures on the imaging results of the imaging points on one side of the dental arch curve. Additionally, the parameters are determined to ensure that the imaging rays change continuously and without abrupt transitions during imaging. The contralateral bony structures mentioned above may include contralateral teeth, surrounding bones, and cervical vertebrae.

In determining the dental arch curve, an appropriate existing dental arch curve can be selected based on the subject's facial shape, or a suitable dental arch curve can be generated by measuring the subject.

Figure 10:
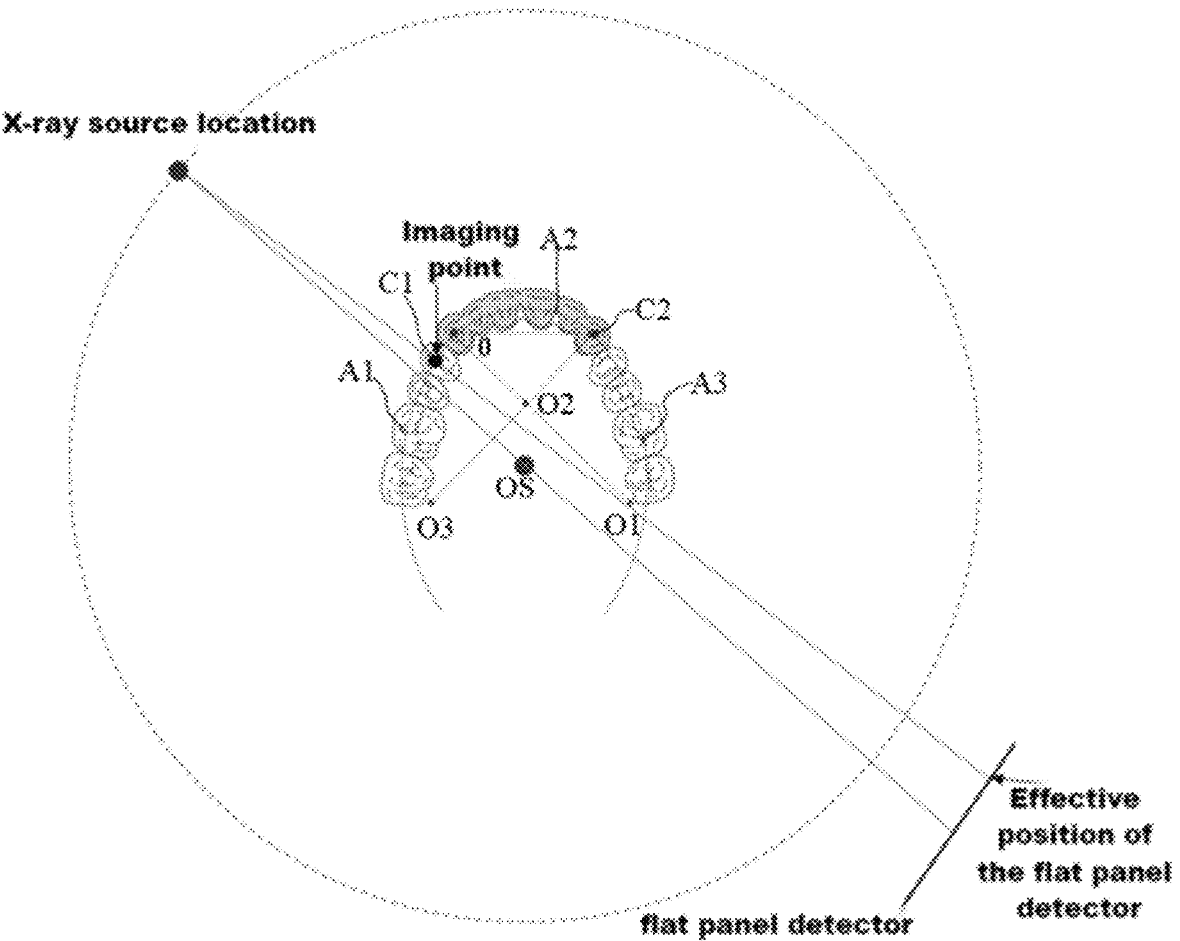
FIG. 10 is a schematic diagram of the determination of the virtual rotation axis parameters according to an embodiment of the present disclosure.

The virtual rotation axis parameters can be the positions of the virtual rotation centers. Those skilled in the art will understand from FIG. 10 that the number of virtual rotation axes can be multiple, for example, three or more. The use of circular arc centers as examples of virtual rotation axis parameters is explained. FIG. 10 shows a schematic diagram of the centers and radii of circular arcs for determining the virtual rotation axis parameters according to one embodiment of the present disclosure. In FIG. 10, the situation of three segments of circular arcs is shown, but the present disclosure is not limited to three segments and can be set according to the situation, such as four segments, five segments, etc.

First, select two reference teeth, namely the first tooth and the second tooth. These reference teeth can be symmetrical teeth, and either upper or lower teeth can be chosen. In FIG. 10, the selected reference teeth are two lower canines. The positions of the first tooth (C1) and the second tooth (C2) can be determined through methods such as laser positioning. Based on the first and second teeth, the dental arch curve is divided into three arc segments: the first arc A1, the second arc A2, and the third arc A3. Based on the subject's facial shape, a dental arch opening control angle θ is specified. The dental arch opening control angle θ can be the angle between the line connecting the positions of the first tooth (C1) and the second tooth (C2), and the line connecting the position C1 or C2 to the center of the second arc A2. Additionally, a dental arch length control coefficient r is determined based on the subject's facial shape. As a result, the centers of the first arc A1, the second arc A2, and the third arc A3 are obtained, denoted as O1, O2, and O3, respectively. The straight-line distance between the center O1 of the first arc A1 and the position C1 of the first tooth is equal to the straight-line distance between the center O3 of the third arc A3 and the position C2 of the second tooth. The straight-line distance between the center O1 of the first arc A1 and the position C1 of the first tooth is also equal to the distance between the positions of the first tooth (C1) and the second tooth (C2) multiplied by the dental arch length control coefficient r, that is: $|O1C1|=|O3C2|=r|C1C2|$. Furthermore, the radii of the first arc A1, the second arc A2, and the third arc A3 can be obtained as r1, r2, and r3, respectively.

Calculating the source corresponding position and the flat-panel detector effective position for each imaging point on the dental arch curve. the flat-panel detector effective position is such that, when imaging a particular point, the source emits X-rays from the source corresponding position, and the flat-panel detector at the flat-panel detector effective position can receive the X-rays to image that point. This effective position also prevents interference from other imaging points affecting the imaging of the specific point (e.g., avoiding other imaging points being imaged at the same effective position or causing image overlap). The effective position is set to only allow imaging of that particular point, while other imaging points cannot be imaged at that position.

During the calculation process, the line connecting the imaging point on the dental arch curve to the center of the arc it lies on is extended. The intersection of this extended line with the source's trajectory is the source corresponding position for that imaging point, and accordingly, the flat-panel detector effective position corresponding to the source corresponding position is obtained. To capture the entire dental arch image, the source can rotate around a fixed rotation center OS while emitting X-rays during the rotation. Then, based on the relationship between the calculated source corresponding position and the flat-panel detector effective position, the X-ray projection data for each imaging point is obtained. The X-ray projection data measured at the flat-panel detector effective position for an imaging point can be a column of data or more than one column of data. For a single column of data, it is measured at the intersection where the extended line from the imaging point to the arc center meets the flat-panel detector, and it can also include one or more columns of data adjacent to this intersection point.

For the imaging point C1 marked in FIG. 10, since it is located on the first arc A1, the line connecting imaging point C1 to the center O1 is extended. The intersection of this extended line with the source's trajectory (dotted circle) determines the source corresponding position. The intersection of this line with the flat-panel detector determines the flat-panel detector effective position. Using the same principle, the source corresponding positions and flat-panel detector effective positions for all imaging points can be obtained. Additionally, for at least some of the imaging points, the line connecting the imaging point to the source, and the line connecting the source to the fixed rotation center form a predetermined angle. This predetermined angle is different for different imaging points. For some imaging points, the line connecting the imaging point to the source may coincide with the line connecting the source to the fixed rotation center.

Rotating the object to be measured around the fixed rotation center OS, X-ray projection data is obtained at the flat-panel detector effective position for each imaging point corresponding to the X-rays emitted from the source corresponding position. The X-ray projection data for the corresponding imaging points is obtained as one or more columns of projection data at the flat-panel detector effective position. After obtaining the projection data columns for each imaging point, the collected projection data columns are reconstructed to obtain the panoramic image of the oral cavity. For example, re-arrangement processing is performed for the first panoramic imaging mode, and the interpolation processing described above is performed for the second panoramic imaging mode.

Figure 11:
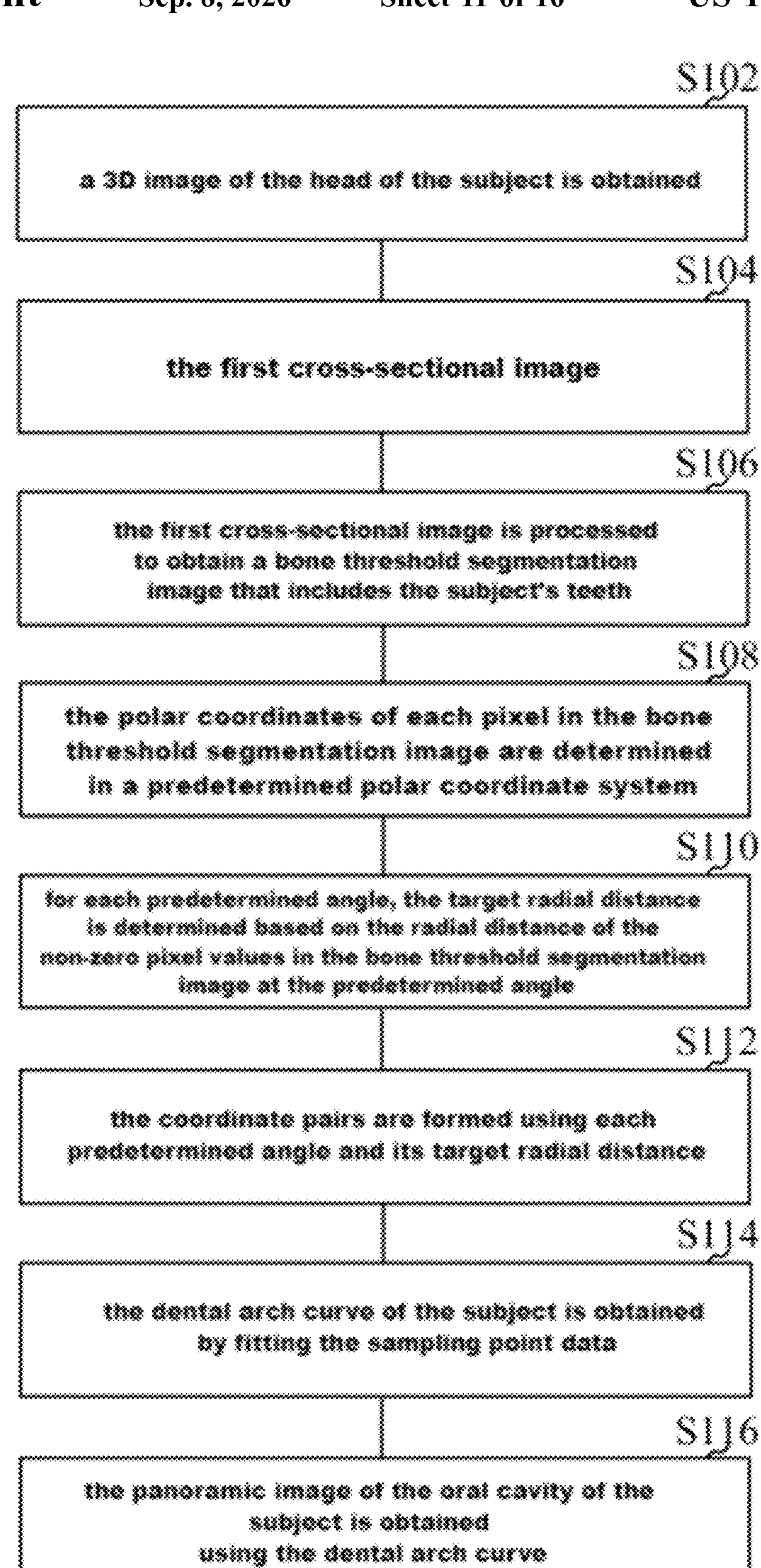
FIG. 11 is a flowchart of the panoramic image generation method according to an embodiment of the present disclosure.

According to another embodiment of this disclosure, a method for generating a panoramic image is also provided. FIG. 11 illustrates a flowchart of the panoramic image generation method. As shown in FIG. 11, the panoramic image generation method may include steps S102 to S116.

In step S102, a 3D image of the head of the subject is obtained. The 3D image of the subject's head can be reconstructed from omnidirectional 2D projection images of the subject's head acquired by a cone-beam X-ray imaging system. The cone-beam X-ray imaging system performs a complete scan of the subject's head to acquire the omnidirectional 2D projection images. The cone-beam X-ray imaging system uses its reconstruction geometric parameters to perform 3D reconstruction of the omnidirectional 2D projection images of the subject's head to obtain a 3D image of the subject's head. The complete scan can be a 180-degree scan or a 360-degree scan of the subject's head. Typically, a 360-degree scan is required when the flat-panel detector of the cone-beam X-ray imaging system is offset to obtain omnidirectional 2D projection images.

In step S104, the first cross-sectional image, which is the dental arch layer in the 3D image, is determined. The first cross-sectional image can be any cross-sectional image in the 3D image that contains the complete dental arch. It can be a cross-sectional image in the 3D image that contains the complete lower dental arch. It can also be a cross-sectional image where the dental arch is most clear or most apparent, or where the dental arch is most dense. As an example, the cross-sectional image corresponding to the Z-axis coordinate in the 3D image at the predetermined dental arch position can be selected as the first cross-sectional image. For example, the predetermined dental arch position can be the upper alveolar bone position or the lower alveolar bone position. In specific applications, the dental arch position can be set as an empirical value through pre-configuration.

In step S104, a pre-trained neural network can be used to process the 3D image to determine the first cross-sectional image. For example, a part or all of the cross-sectional images in the 3D image can be input into the pre-trained neural network, which outputs the confidence level for each cross-sectional image, indicating the probability that the cross-sectional image is the first cross-sectional image. The cross-sectional image with the highest confidence level can be selected as the first cross-sectional image, or the middle layer of multiple cross-sectional images with a confidence level greater than a predetermined threshold can be selected as the first cross-sectional image.

The neural network used to determine the first cross-sectional image can be trained using samples marked as the densest cross-sectional image of the dental arch and all cross-sectional images of the corresponding 3D image. The neural network can be, but is not limited to, a convolutional neural network, a feedforward neural network, or other types. The architecture and type of the neural network are not limited in this embodiment of the disclosure.

Additionally, in step S104, the user can select the clearest layer of the dental arch in the 3D image as the first cross-sectional image in response to user operation. That is, manually selecting the clearest cross-sectional image of the dental arch in the 3D image as the first cross-sectional image.

In step S106, the first cross-sectional image is processed to obtain a bone threshold segmentation image that includes the subject's teeth. Specifically, bone threshold segmentation and Gaussian smoothing processing are performed on the first cross-sectional image to obtain a bone threshold segmentation image that includes the subject's teeth. By performing bone threshold segmentation on the first cross-sectional image, substances such as soft tissue and water in the first cross-sectional image can be removed to obtain a bone threshold segmentation image that includes only bones and teeth. Performing Gaussian smoothing on the bone threshold segmentation image can remove noise from the bone threshold segmentation image, thereby obtaining a more accurate and higher-quality bone threshold segmentation image. This can improve the quality of the bone threshold segmentation image and thereby increase the accuracy of the dental arch curve.

In step S108, the polar coordinates of each pixel in the bone threshold segmentation image are determined in a predetermined polar coordinate system. Specifically, each pixel in the bone threshold segmentation image can be mapped to the predetermined polar coordinate system through the conversion relationship from the Cartesian coordinate system to the polar coordinate system, thereby obtaining the polar coordinate representation of each pixel's position in the bone threshold segmentation image. For example, the predetermined polar coordinate system can be, but is not limited to, a polar coordinate system with the centroid of the bone threshold segmentation image as the pole.

In step S110, for each predetermined angle, the target radial distance is determined based on the radial distance of the non-zero pixel values in the bone threshold segmentation image at the predetermined angle. The predetermined angles include multiple angles at intervals of a predetermined value between 0 degrees and 360 degrees. In specific applications, suitable predetermined angles can be selected as needed. Step S110 can include the following content. Step a1, determine the first pixel with the smallest radial distance and the second pixel with the largest radial distance among the non-zero pixel values in the bone threshold segmentation image at the first predetermined angle. On the polar axis of the first predetermined angle, radiate outward from the pole of the polar coordinate system. The first non-zero pixel value is the first pixel, and the last non-zero pixel value is the second pixel. Since the pixel values of parts other than bones and teeth in the bone threshold segmentation image are all set to zero by default, and the pixel values of the pixels belonging to the teeth are non-zero, in this way, the frontmost and rearmost pixel points of the teeth can be located accurately (i.e., the first pixel and the second pixel), thus accurately positioning the tooth area. The first predetermined angle refers to any predetermined angle. Step a2, take the average of the radial distances of the first pixel and the second pixel as the target radial distance for the first predetermined angle. Taking the average of the radial distances of the first and second pixels as the target radial distance can accurately locate the sampling point in the middle region of the teeth. Since the dental arch is most apparent and complete in the middle region of the teeth, determining the sampling point in this way can further increase the accuracy of the dental arch curve.

In step S112, the coordinate pairs are formed using each predetermined angle and its target radial distance, resulting in a sequence of coordinate pairs, which serve as the sampling point data for the dental arch curve. Each sampling point is a point in the predetermined polar coordinate system with the predetermined angle as the polar angle and the target radial distance of the predetermined angle as the radial distance.

In some embodiments, each coordinate pair in the sequence of coordinate pairs can be arranged in ascending order of their corresponding predetermined angles. For example, if 36 predetermined angles are selected in advance, the sequence of coordinate pairs will contain 36 coordinate pairs, with each coordinate pair including the angle value of the predetermined angle and its corresponding target radial distance.

In step S114, the dental arch curve of the subject is obtained by fitting the sampling point data. In some embodiments, polynomial fitting methods can be used to fit the dental arch curve using the sampling point data. For example, 5th-degree, 6th-degree, or 8th-degree polynomials can be used to achieve the fitting of the dental arch curve.

Using a 5th-degree polynomial as an example, the dental arch curve can be fitted according to the following equation (1):

$$r = a_0 + a_1\theta + a_2\theta^2 + a_3\theta^3 + a_4\theta^4 + a_5\theta^5 \quad (1)$$

Wherein, r represents the target radial distance corresponding to the predetermined angle, and θ represents the predetermined angle, $a_0$, $a_1$, $a_2$, $a_3$, $a_4$, as both of which are coefficients.

Specifically, by substituting five pairs of numerical values from the sequence into equation (1), a system of equations is formed. The coefficient $a_0$, $a_1$, $a_2$, $a_3$, $a_4$, $a_5$ in equation (1) is then determined through the method of least squares. Using the predetermined angle as a variable, equation (1) is recalculated to determine anew the target radial distance corresponding to each predetermined angle, and these recalculated values are updated within the sequence of numerical pairs. Finally, the updated sequence of numerical pairs is used to derive the dental arch curve.

Mapping the bone threshold segmentation image to a polar coordinate system and using polynomial fitting allows for achieving a dental arch curve with higher accuracy.

In step S116, the panoramic image of the oral cavity of the subject is obtained using the dental arch curve. Specifically, step S116 may include the following steps b1 to b4. Step b1, for each point on the dental arch curve, calculates the X-ray passing through this point during imaging and obtains the projection data of the X-ray on the flat-panel detector. The source-subject point-corresponding point on the flat-panel detector form a straight line. Step b2, the projection data of the X-ray passing through the point is weighted and accumulated to obtain the imaging value of the point. In this way, one line of data can be obtained from a dental arch curve. Step b3, the dental arch curve is moved vertically up and down to obtain multiple lines of data. By arranging all lines in sequence, a complete panoramic image of the oral cavity is obtained.

Figure 12:
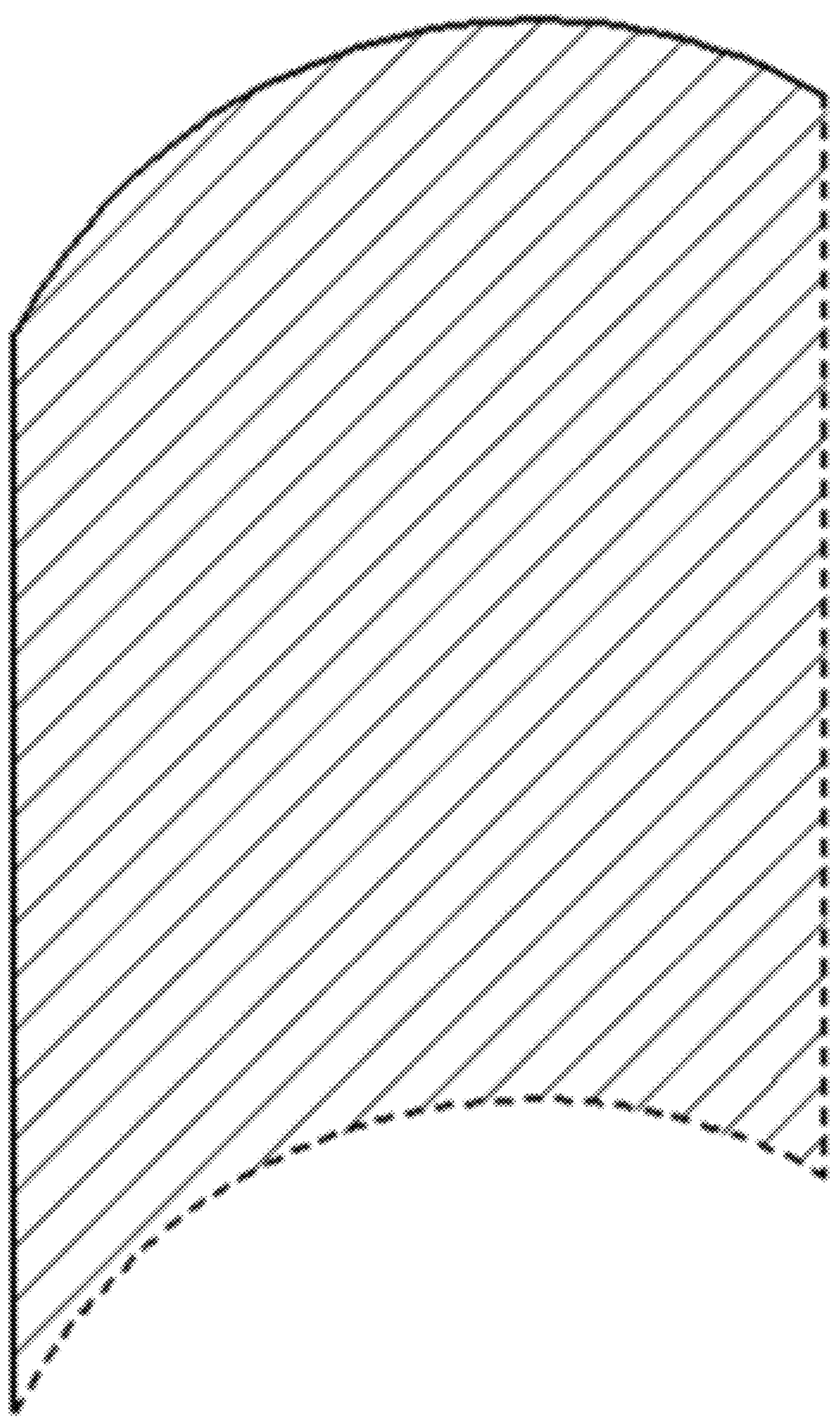
FIG. 12 is an exemplary diagram of the target dental arch surface according to an embodiment of the present disclosure.

In some embodiments, step S116 may include the following steps c1 to c2. Step c1, using the dental arch curve as the generatrix and the Z-axis of the three-dimensional image as the baseline, determines the target dental arch surface. The Z-axis is perpendicular to the first cross-sectional image. FIG. 12 shows an example diagram of the target dental arch surface. Step c2, the dental arch surface is unfolded to obtain the panoramic image of the oral cavity of the subject.

Additionally, other applicable methods can be used in step S116 to obtain the panoramic image of the oral cavity using the dental arch curve. The specific implementation methods of step S116 are not limited in this disclosure.

The embodiment of FIG. 11 combines a more accurate dental arch curve with the above-described method to obtain panoramic images of the oral cavity. This approach not only achieves true panoramic imaging of the oral cavity without increasing mechanical structures but also enhances the accuracy of panoramic images. It brings the quality of panoramic images closer to that of panoramic imaging machines, surpassing their image quality. Additionally, it supports flexible selection of cross-sectional views, allowing users to adjust the shape and position of the oral panoramic image according to their needs. Through the embodiment of FIG. 11, both CT images and oral panoramic images can be obtained in a single scan. The cross-sectional images can be flexibly chosen, facilitating precise specification and real-time adjustment of the shape and position of the oral panoramic image. This capability not only effectively avoids issues such as the inability of preset scanning trajectories to match the actual dental arch of the subject, rendering panoramic images unusable, but also enhances clinical utility.

The disclosed imaging system achieves a three-in-one oral cavity capture based on circular trajectory. It enables CBCT, panoramic images, and cephalometric imaging on a circular trajectory X-ray imaging system. Furthermore, it simulates multi-rotation center panoramic imaging, achieving better fitting of the dental arch surface. The disclosed cone beam X-ray imaging system realizes genuine panoramic image capture of the oral cavity without increasing mechanical structures, unlike reconstructed data composite panoramic imaging. Therefore, it offers faster imaging speed and requires lower geometric control during imaging.

The imaging system has only one rotation center, fewer moving parts, and a simple structure, requiring only one flat-panel detector and one X-ray source. The imaging mode can involve keeping the X-ray source and flat-panel detector stationary while the subject rotates, reducing machine control requirements and minimizing head movement offsets of the subject. This can reduce the probability of reconstruction artifacts, improving precision and image interpretation to better assist doctors in patient assessment.

Those skilled in the art should understand that with the disclosed imaging system, it is possible to perform oral CT mode imaging, oral panoramic mode imaging, and cephalometric mode imaging. In the case of CT mode imaging selection, the imaging system can directly capture the subject. In the case of oral panoramic mode imaging selection, the imaging system first initiates a rapid positioning mode for imaging. Based on the positioning results of the rapid positioning mode, the imaging system performs adaptive positioning and then proceeds with oral panoramic mode imaging. During the adaptive positioning process, the dental arch curve of the subject needs to be determined and adaptive positioning needs to be performed based on the determined dental arch curve, as described above. Circular trajectory technology is then used to complete the oral panoramic mode imaging.

In the case of cephalometric mode imaging selection, the imaging system first initiates a rapid positioning mode for imaging. Based on the positioning results of the rapid positioning mode, the imaging system performs adaptive positioning and then proceeds with cephalometric mode imaging. As shown in FIG. 1, the imaging system may include a positioning control device 110. The control device 400 can control the positioning control device 110 to adjust the height of the source and control the rotation device to achieve adaptive positioning of the imaging system.

The rapid positioning mode uses low-dose X-rays and fast scanning to achieve rapid positioning, assisting in confirming positioning. The rapid positioning mode can use the same motion trajectory as the oral CT mode imaging. The difference from the oral CT mode imaging lies in lower X-ray dosage, faster rotation speed, fewer projections, and larger reconstruction pixels. The rapid positioning mode can outline the subject, reconstruct the outline of the subject's head and dental arch, with no high requirements for image spatial resolution and contrast resolution. It requires lower reconstruction pixel quality, radiation dose, and anti-aliasing requirements. Therefore, it can employ lower radiation dose, fewer projection images, faster rotation process, and larger pixels for reconstruction. For example, if the oral CT mode imaging uses 600 projection images, each with an exposure time of 8 ms, a rotation cycle of 30 seconds, and a reconstruction pixel of 0.25 mm, then the rapid positioning mode can use 200 projection images, an exposure time of 2 ms, a rotation cycle of 5 seconds, and a reconstruction pixel of 0.5 mm.

Figure 13:
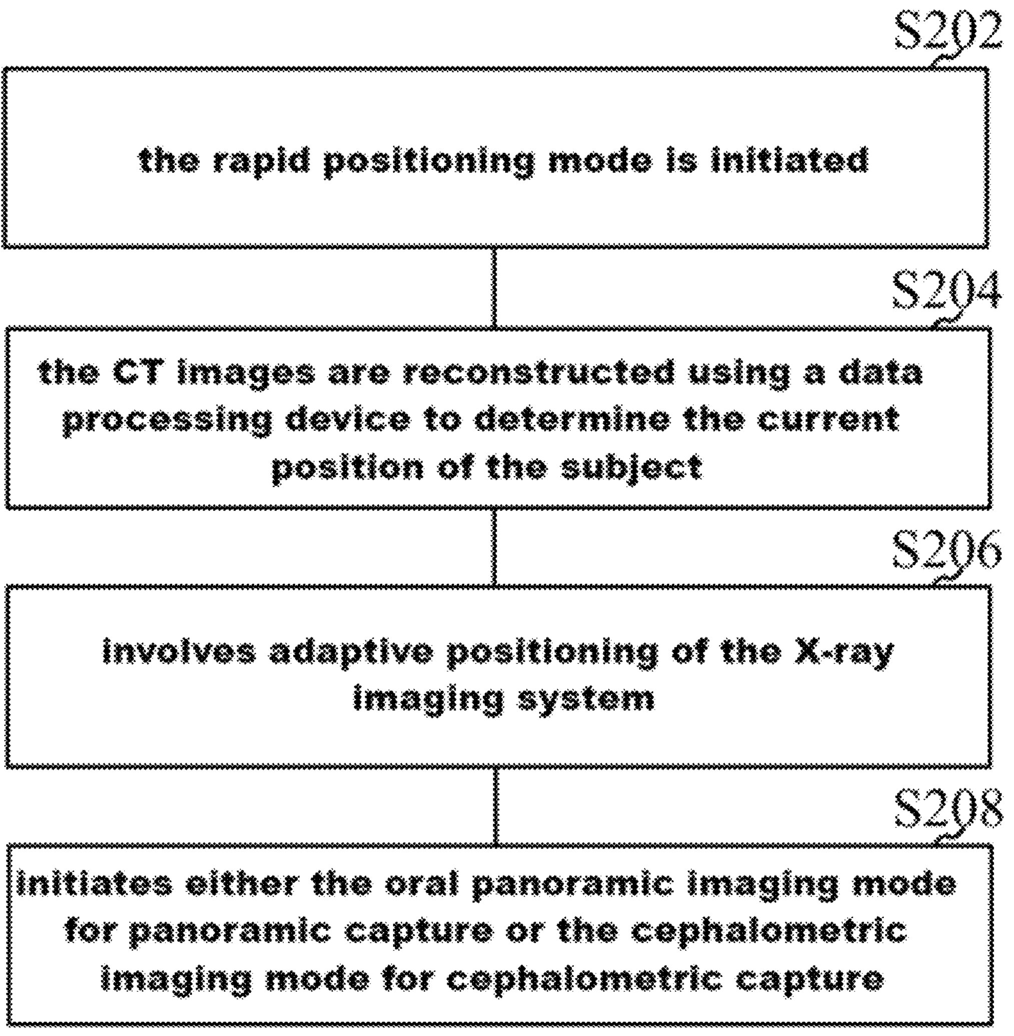
FIG. 13 is a flowchart of the rapid positioning method according to an embodiment of the present disclosure.
Figure 14:
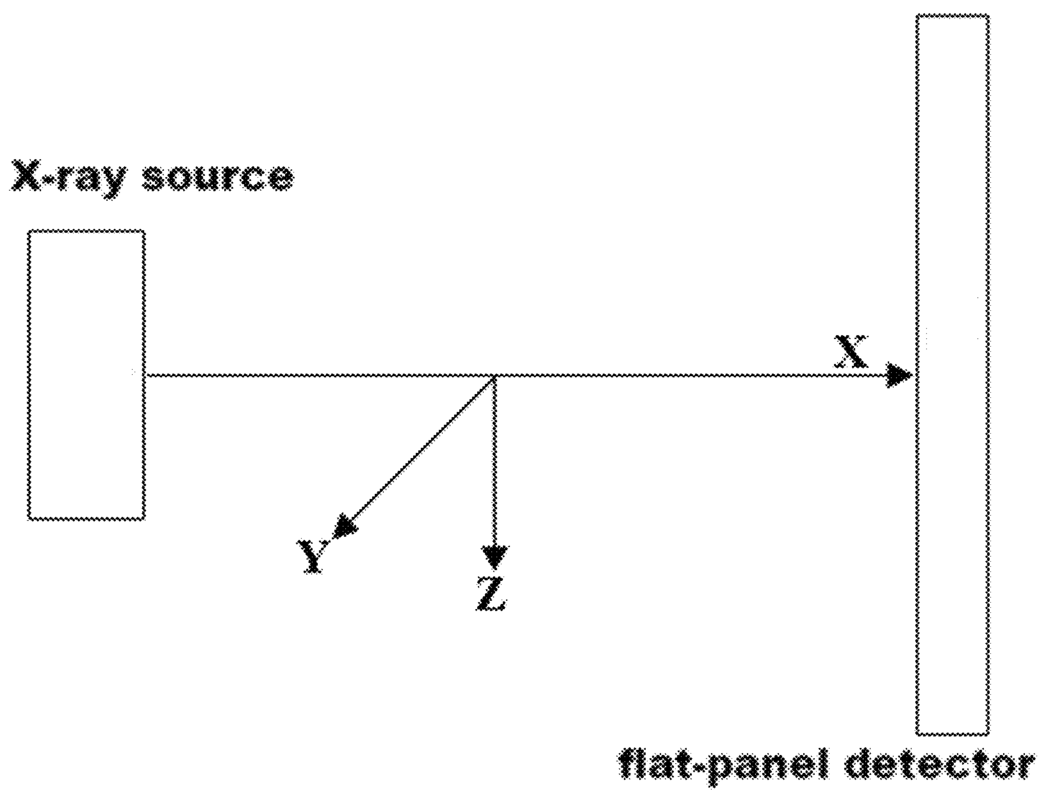
FIG. 14 is a schematic diagram of the X-ray source adjustment according to an embodiment of the present disclosure.

Based on further embodiments disclosed herein, a rapid positioning method based on the imaging system described is provided. FIG. 13 illustrates the flowchart of this rapid positioning method.

In Step S202, the rapid positioning mode is initiated, where quick low-dose imaging takes place. In Step S204, the CT images are reconstructed using a data processing device to determine the current position of the subject. Step S206 involves adaptive positioning of the X-ray imaging system, such as adjusting the source height and controlling the rotation device. Step S208 initiates either the oral panoramic imaging mode for panoramic capture or the cephalometric imaging mode for cephalometric capture, resulting in panoramic or cephalometric images.

Additionally, before Step S202, there may be a step to select the imaging mode. For example, if the user selects the oral panoramic imaging mode or the cephalometric imaging mode, then Step S202 is executed. However, if the oral CT mode is chosen, the system proceeds directly to oral CT imaging.

In the case of initiating the rapid positioning mode based on the oral panoramic imaging mode, in Step S206, the current dental arch curve of the subject can be obtained through reconstructed CT images. This enables the X-ray imaging system to adjust autonomously based on the required position for imaging, as discussed in related content such as FIG. 10.

In the case of initiating the rapid positioning mode based on the cephalometric imaging mode, in Step S206, adjustment of the positioning can be facilitated using the aforementioned positioning control device 110. For instance, this involves vertical movement of the source to adjust its height and controlling the rotation device's rotation. After reconstructing the CT images to obtain the CT model, data analysis calculates three spatial angles relative to the standard position of the subject (pitch, yaw, roll). Pitch refers to the tilt angle along the X-axis, yaw refers to the rotation angle along the Y-axis, and roll refers to the rotation angle along the Z-axis. These three angular measurements can be fed back to the control device, which then adjusts the positioning control device for adaptive positioning. During the adaptive positioning process, the subject remains stationary (sitting still on the rotation device), and adjustments are made using the positioning control device. Initially, the roll angle can be adjusted for alignment, followed by adjustments to the yaw angle. After completing the capture, a final image rotation can be performed to adjust the pitch angle. Once adjustments are completed, the cephalometric imaging mode capture can proceed.

Figure 15:
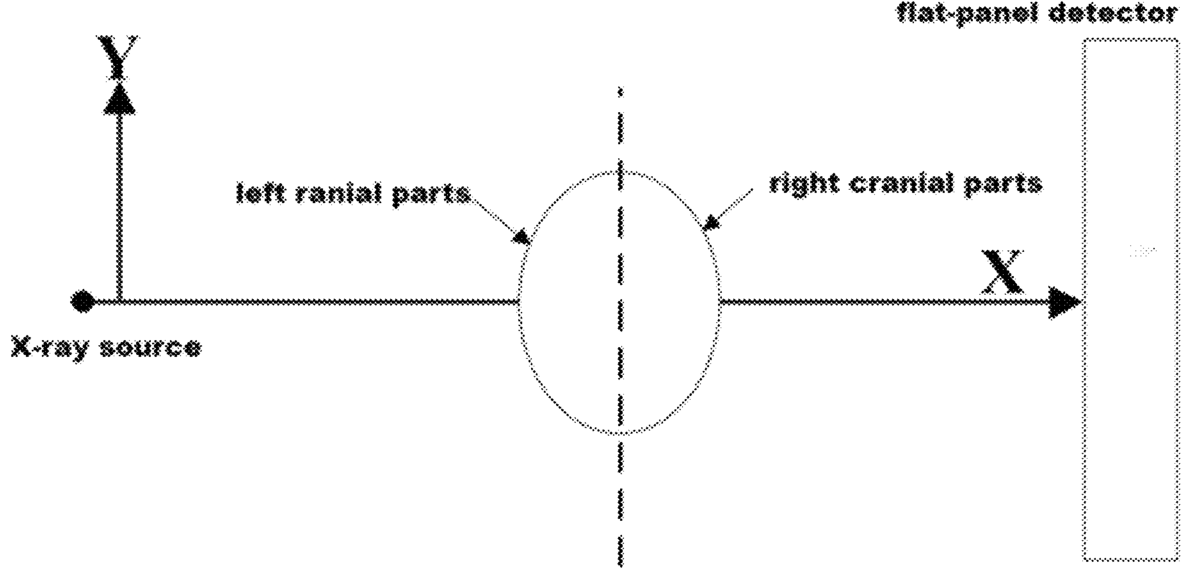
FIG. 15 is a schematic diagram of the state after adjusting the roll angle according to an embodiment of the present disclosure.

After reconstructing the CT images obtained from the rapid positioning mode, the roll angle of the subject's skull relative to the standard position is determined. Based on this roll angle, the subject is rotated using the rotation drive device so that the left and right sides of the skull approximate symmetry, as depicted in FIG. 15. The skull is divided into left and right parts using a line passing through the center of the subject's skull. When the subject is correctly positioned, these left and right parts of the skull will approximate symmetry. During the calculation of the roll angle, the subject's head is projected along the X-axis, and clearer projection images indicate greater symmetry between the left and right parts of the skull. Therefore, the angle $\alpha$ (where a E $(-\pi/2, \pi/2)$) of skull rotation is determined such that the forward projection gradient variation is minimized.

Figure 16:
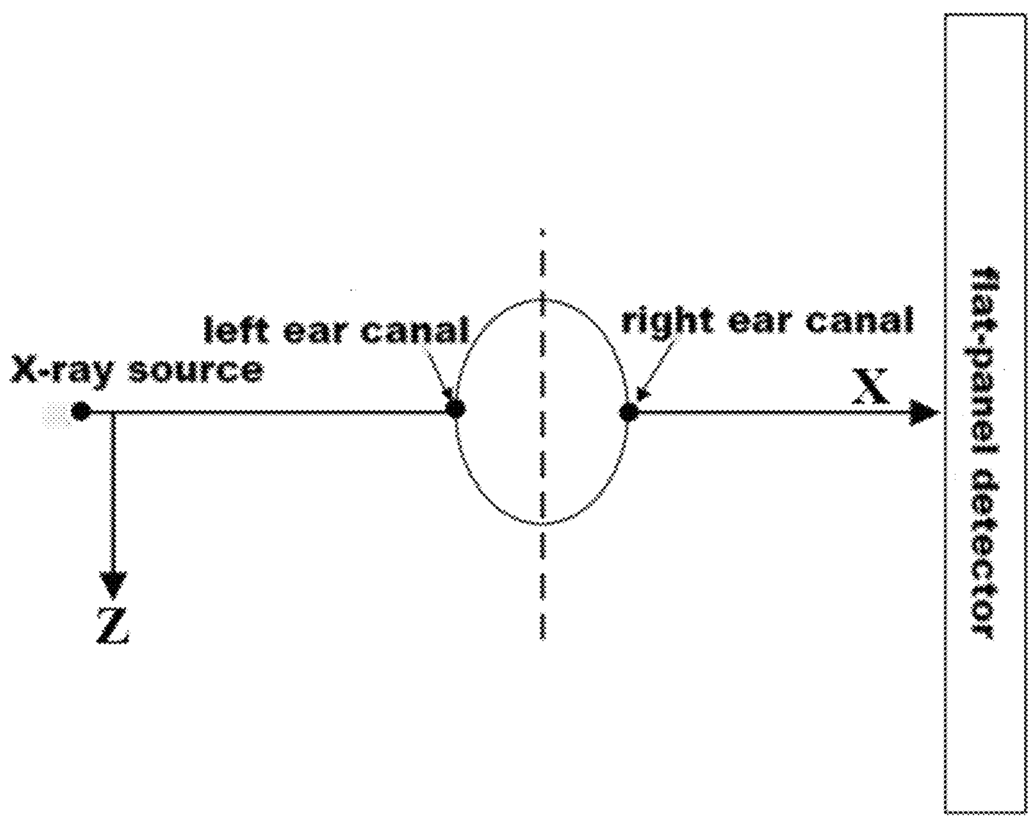
FIG. 16 is a schematic diagram of the state after adjusting the yaw angle according to an embodiment of the present disclosure.

After reconstructing the CT images from the rapid positioning mode, the yaw angle of the subject's skull relative to the standard position is determined. Based on the roll angle obtained, adaptive positioning can be achieved by moving the position of the source. After calculating the yaw angle, the target coordinates of the source are determined, and then the source is moved to align with a straight line passing through the source, left ear canal, and right ear canal, as shown in FIG. 16.

Calculation of Yaw Angle Based on Collinearity of X-ray Source, Left Ear Canal, and Right Ear Canal. To calculate the yaw angle ensuring that the X-ray source, left ear canal, and right ear canal are collinear, the roll angle is adjusted first. Therefore, it can be assumed that the Y-coordinates of the left ear canal and the right ear canal are the same or approximately the same. At this point, only the (X, Z) coordinates need to be considered. Assume the coordinates of the left ear canal are (X1, Y, Z1), the coordinates of the right ear canal are (X2, Y, Z2), and the coordinates of the X-ray source are (X3, Y3, Z3). To ensure the X-ray source, left ear canal, and right ear canal are collinear, the coordinates of the X-ray source need to be $$\left(X_3, Y_1, \frac{X_3 - X_1}{X_2 - X_1} * (Z_2 - Z_1) + Z_1\right)$$

The distance the X-ray source needs to move in the Y-direction is (Y-Y3). The distance the X-ray source needs to move in the Z-direction is given as $$\frac{X_3 - X_1}{X_2 - X_1} * (Z_2 - Z_1) + Z_1 - Z_3$$

By determining the distances the X-ray source needs to move in the Y and Z directions, the X-ray source can be adjusted to ensure it is collinear with the left ear canal and right ear canal, thereby completing the adaptive positioning.

Because the pitch angle does not affect the image quality of the lateral view, the angle of the image can be adjusted after the shooting is completed. For example, the angle of the image can be rotated based on the alignment of the teeth parallel to the horizontal plane.

The above description pertains to pose confirmation during lateral view imaging. After confirming the pose for the lateral view imaging, the shooting of the frontal view images can be conducted based on the adjusted pose from the lateral view.

In this disclosure, the calculation of the three spatial angles can be achieved through the angle calculation unit of the data processing device 300.

Figure 17:
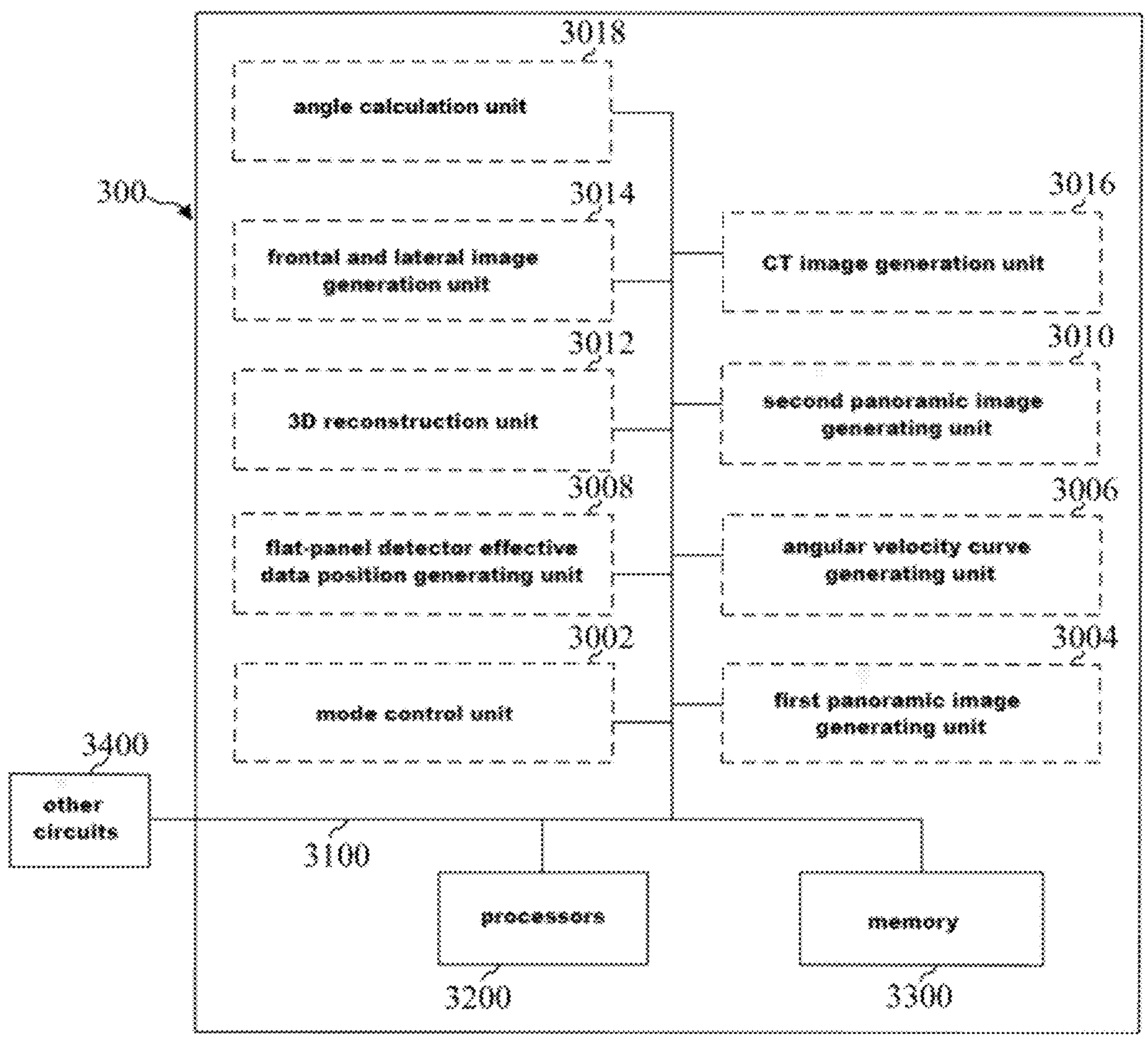
FIG. 17 is a block diagram illustrating the structure of the data processing device according to an embodiment of the present disclosure.

The data processing device 300 of the present disclosure can be implemented in the form of computer software architecture or hardware architecture based on processing systems. FIG. 17 illustrates a schematic block diagram of an embodiment of the data processing device 300 implemented using hardware architecture in the present disclosure. The data processing device 300 may include various modules that execute the respective steps in the above flowchart, such as mode control unit 3002, first panoramic image generation unit 3004, angular velocity curve generation unit 3006, flat-panel detector effective data position generation unit 3008, second panoramic image generation unit 3010, 3D reconstruction unit 3012, frontal and lateral image generation unit 3014, CT image generation unit 3016, and angle calculation unit 3018, among others. Therefore, each step or combination of steps in the flowchart can be performed by corresponding modules, and the device may include one or more of these modules.

The hardware architecture can utilize a bus architecture. The bus architecture may include any number of interconnecting buses and bridges, depending on the specific application of the hardware and overall design constraints. The bus 3100 connects various circuits, such as one or more processors 3200, memory 3300, and/or various hardware modules. The bus 3100 may also connect various other circuits 1400, such as peripheral devices, voltage regulators, power management circuits, external antennas, etc.

The bus 3100 can be an Industry Standard Architecture (ISA) bus, Peripheral Component Interconnect (PCI) bus, or Extended Industry Standard Architecture (EISA) bus, among others. The bus can be divided into address buses, data buses, control buses, etc. For ease of representation, only one connection line is shown in the diagram, but it does not imply that there is only one bus or one type of bus.

Any process or method description represented in the flowchart or otherwise described here can be understood as including executable instructions in the form of code modules, segments, or parts that implement specific logical functions or processes. The scope of the preferred embodiments of the present disclosure includes additional implementations where functions may be performed in an order other than as shown or discussed, including performing functions concurrently according to the functions involved. Processors execute various methods and processes described above. For example, embodiments of methods disclosed herein can be implemented as software programs that are tangibly included in machine-readable media, such as memory. In some embodiments, all or part of the software program may be loaded and/or installed via memory and/or communication interfaces. When the software program is loaded into memory and executed by a processor, one or more steps of the methods described above may be executed.

In other embodiments, the processor may be configured to perform one of the above methods in any appropriate manner (e.g., using firmware). The logical and/or steps represented in the flowchart or otherwise described here may be specifically implemented in any readable storage medium for use by instruction execution systems, devices, or equipment (such as computer-based systems including processors or other systems capable of fetching instructions and executing them).

As used herein, "machine-readable media" may refer to devices that may include, store, communicate, broadcast, or transmit programs for use by instruction execution systems, devices, or equipment, or combined with these instruction execution systems, devices, or equipment. More specific examples (non-exhaustive list) of machine-readable media include electronic devices with one or more wiring (electronic devices), portable computer disk boxes (magnetic devices), random access memory (RAM), read-only memory (ROM), erasable Programmable Read Only Memory (EPROM or flash memory), fiber devices, and portable read-only memory (CD-ROM). In addition, machine-readable media may even be paper or other suitable media on which programs may be printed for use as electronic programs, for example, by optical scanning of paper or other media, followed by editing, decoding or processing as needed. In an appropriate manner, the program is obtained electronically and then stored in memory.

It should be understood that various parts of the present disclosure may be implemented in hardware, software, or combinations thereof. In the embodiments described above, multiple steps or methods may be implemented using software stored in memory and executed by suitable processors. For example, if implemented in hardware, as in another embodiment, one or more of the following techniques known in the art may be used individually or in combination to implement the methods described herein: discrete logic circuits with logic gate circuits for implementing logical functions on data signals, dedicated integrated circuits with suitable combinations of logic gate circuits, programmable gate arrays (PGA), field programmable gate arrays (FPGA), etc.

Those skilled in the art will appreciate that all or part of the steps of the above embodiments may be performed by hardware or software configured to execute the corresponding functions. In the embodiments disclosed herein, the steps or methods represented in the flowchart or otherwise described herein may specifically be implemented in any readable storage medium for use by instruction execution systems, devices, or equipment, or in combination with these instruction execution systems, devices, or equipment.

Furthermore, in the various embodiments of the present disclosure, each functional unit can be integrated into a single processing module, can exist as individual physical units, or two or more units can be integrated into one module. The integrated module can be implemented in the form of hardware, or it can be implemented in the form of software function modules. If the integrated module is implemented in the form of software function modules and sold or used as an independent product, it can also be stored in a readable storage medium. The storage medium can be read-only memory, a disk, an optical disk, etc.

Those skilled in the art should understand that the above embodiments are provided for the purpose of illustrating the present disclosure clearly, and are not intended to limit the scope of the present disclosure. Various changes or modifications can be made based on the above disclosure by those skilled in the art, and such changes or modifications are still within the scope of the present disclosure.

What is claimed is:

1. An oral cone-beam X-ray imaging system, wherein working modes of the oral cone-beam X-ray imaging system include an oral CT imaging mode, an oral panoramic imaging mode, and a cranial lateral imaging mode, the oral cone-beam X-ray imaging system comprising:

an X-ray source, configured to emit cone-beam X-rays towards an object being measured;

a flat-panel detector, configured to detect the X-rays passing through the object being measured;

a rotation drive device, configured to rotate the X-ray source and the flat-panel detector, or to control the rotation device to rotate the object being measured;

a data processing device, configured to receive a working mode instruction to select a set of working mode control parameters corresponding to one of the oral CT imaging mode, the oral panoramic imaging mode, and the cranial lateral imaging mode; and a control device, configured to receive the set of working mode control parameter set, control the rotation drive device, and control the X-ray source and the flat-panel detector to perform imaging, wherein a quantity of the X-ray source, the flat-panel detector, and the rotation drive device is one, forming a single-channel imaging system, wherein the working modes further include a quick positioning mode, and the data processing device is configured to select the quick positioning mode based on receiving another one working mode instruction, in the quick positioning mode, an imaging trajectory of the oral CT imaging mode is adopted, and a radiation dose of the X-rays in the quick positioning mode is lower than that of the X-rays in oral CT imaging mode, so as to perform adaptive positioning of the imaging system based on positioning results of the quick positioning mode.

2. The oral cone-beam X-ray imaging system according to claim 1, wherein a rotation speed controlled by the rotation drive device in the quick positioning mode is faster than that in the oral CT imaging mode, and/or a reconstruction pixel size in the quick positioning mode is larger than that in the oral CT imaging mode.

3. The oral cone-beam X-ray imaging system according to claim 1, further comprising a positioning control device, wherein based on the positioning results, the positioning control device adjusts a height of the X-ray source and controls the rotation device to rotate according to a roll angle and a yaw angle calculated from the imaging of the quick positioning mode, so as to achieve the adaptive positioning.

4. The oral cone-beam X-ray imaging system according to claim 3, wherein after selecting the oral panoramic imaging mode and performing the adaptive positioning, the data processing device obtains a dental arch curve of the object being measured and determines virtual rotation axis parameters, based on the virtual rotation axis parameters, it calculates the corresponding positions of the X-ray source and the effective positions of the flat-panel detector for each imaging point on the dental arch curve, the rotation drive device rotates the object being measured, so that during the imaging process along the circular trajectory, X-ray projection data at the effective position of the flat-panel detector corresponding to each imaging point is acquired from the corresponding position of the X-ray source, the data processing device processes the X-ray projection data corresponding to each imaging point to obtain the oral panoramic image.

5. The oral cone-beam X-ray imaging system according to claim 4, wherein the data processing device is configured to:

obtain a three-dimensional image of the measured part of the object being measured;

determine a first cross-sectional image, which is the dental arch layer in the three-dimensional image;

process the first cross-sectional image to obtain a bone threshold segmentation image that includes the teeth of the object being measured;

determine the polar coordinates of each pixel in the bone threshold segmentation image in a predetermined polar coordinate system;

determine the target radius corresponding to each predetermined angle based on the radial distances of non-zero pixel values at the predetermined angle in the bone threshold segmentation image;

form a sequence of value pairs with each predetermined angle and its target radius, where the sequence of value pairs constitutes the sampling point data of the dental arch curve; and fit the dental arch curve of the object being measured using the sampling point data.

6. The oral cone-beam X-ray imaging system according to claim 5, wherein the data processing device is configured to:

use the cross-sectional image at the Z-axis coordinate corresponding to the predetermined dental arch position in the three-dimensional image as the first cross-sectional image; or utilize a pre-trained neural network to process the three-dimensional image to determine the first cross-sectional image.

7. The oral cone-beam X-ray imaging system according to claim 5, wherein the data processing device is configured to:

perform bone threshold segmentation and Gaussian smoothing on the first cross-sectional image to obtain a bone threshold segmentation image that includes the teeth of the object being measured.

8. The oral cone-beam X-ray imaging system according to claim 5, wherein the data processing device is configured to:

determine, in the bone threshold segmentation image, the first pixel with the smallest radial distance and the second pixel with the largest radial distance among the non-zero pixel values at a first predetermined angle;

use the average radial distance of the first pixel and the second pixel as the target radial distance for the first predetermined angle.

9. The oral cone-beam X-ray imaging system according to claim 4, wherein the data processing device is configured to:

for each imaging point on the dental arch curve, calculate the X-ray passing through the imaging point during the imaging process and obtain the projection data of the X-ray on the flat-panel detector;

accumulate the projection data of the X-ray passing through the imaging point by weight to obtain the imaging value of the imaging point, resulting in a row of data for the dental arch curve; and move the dental arch curve up and down in the vertical direction to obtain multiple rows of data, and arrange these multiple rows of data in sequence to obtain a complete oral panoramic image.

10. The oral cone-beam X-ray imaging system according to claim 1, wherein a Source-to-Image Distance between the X-ray source and the flat-panel detector is 1.5 meters to 2.5 meters, and a difference between the Source-to-Image Distance and a Source-to-Axis Distance between the X-ray source and the rotation axis is 0.2 meters to 0.4 meters.

11. The oral cone-beam X-ray imaging system according to claim 10, wherein the Source-to-Image Distance is 1.7 meters, and the difference between the Source-to-Image Distance and the Source-to-Axis Distance is 0.25 meters.

12. The oral cone-beam X-ray imaging system according to claim 1, wherein the rotation drive device rotates the object being measured, so that the X-ray source and the flat-panel detector perform imaging along a circular trajectory around a fixed rotation center relative to the object which is rotated.

13. The oral cone-beam X-ray imaging system according to claim 12, wherein:

the oral panoramic imaging mode includes a first oral panoramic imaging mode, wherein the object being measured is rotated so that the imaging is performed with variable-speed rotation along the circular trajectory; and/or the oral panoramic imaging mode includes a second oral panoramic imaging mode, wherein the object being measured is rotated so that the imaging is performed with constant-speed rotation along the circular trajectory.

14. The oral cone-beam X-ray imaging system according to claim 13, wherein:

in the first oral panoramic imaging mode, a series of two-dimensional projection data is acquired through the flat-panel detector, and the data processing device performs reordering processing on the series of two-dimensional projection data to generate a first panoramic image;

in the second oral panoramic imaging mode, a series of two-dimensional projection data is acquired through the flat-panel detector, and the data processing device performs interpolation processing on the series of two-dimensional projection data to generate a second panoramic image.

15. A quick positioning method based on the oral cone-beam X-ray imaging system according to claim 1, comprising:

activating the quick positioning mode and emitting low-dose X-rays;

receiving and reconstructing CT images to obtain the current pose of the object being measured; and based on the current pose, performing the adaptive positioning of the oral cone-beam X-ray imaging system to conduct imaging in the oral panoramic imaging mode or the cranial lateral imaging mode.

16. The quick positioning method according to claim 15, wherein a rotation speed controlled by the rotation drive device in the quick positioning mode is faster than the rotation speed controlled by the rotation drive device in the oral CT imaging mode; and/or the reconstruction pixel size in the quick positioning mode is larger than the reconstruction pixel size in the oral CT imaging mode.

17. The quick positioning method according to claim 15, wherein, when it is necessary to select the oral panoramic imaging mode for imaging, the quick positioning mode is activated, and the CT images are reconstructed to obtain the current dental arch curve of the object being measured, this allows the adaptive positioning of the imaging system based on the current dental arch curve and the required pose for imaging.

18. The quick positioning method according to claim 15, wherein, when it is necessary to select axial and a cranial lateral cephalometric imaging mode for imaging, the quick positioning mode is activated, and the CT images are reconstructed to obtain a yaw angle and/or a roll angle of a cranium of the object who is detected relative to a standard position, the adaptive positioning of the oral cone-beam X-ray imaging system is performed by adjusting the yaw angle and/or the roll angle.

19. The quick positioning method according to claim 18, wherein:

based on the obtained roll angle, the rotation drive device rotates the object being measured so that left and right cranial parts of the object are symmetrical, where a straight line passing through the center of the cranium divides it into the left and right cranial parts; and/or based on the obtained yaw angle, the position of the X-ray source is adjusted so that the X-ray source, a left ear canal, and a right ear canal of the object being measured are collinear.

* * * * *